US007557100B2

(12) United States Patent
Johnson et al.

(10) Patent No.: US 7,557,100 B2
(45) Date of Patent: Jul. 7, 2009

(54) ANTIBACTERIAL AGENTS

(75) Inventors: Timothy A. Johnson, Howell, MI (US); Dennis J. McNamara, Ann Arbor, MI (US); Debra A. Sherry, Chelsea, MI (US); Peter Laurence Toogood, Ann Arbor, MI (US)

(73) Assignee: Pfizer Inc., New York, NY (US)

( * ) Notice: Subject to any disclaimer, the term of this patent is extended or adjusted under 35 U.S.C. 154(b) by 163 days.

(21) Appl. No.: 11/641,215

(22) Filed: Dec. 19, 2006

(65) Prior Publication Data

US 2007/0197518 A1    Aug. 23, 2007

Related U.S. Application Data

(60) Provisional application No. 60/753,262, filed on Dec. 22, 2005.

(51) Int. Cl.
*C07D 498/20*    (2006.01)
*A61K 31/5386*   (2006.01)

(52) U.S. Cl. ...................... 514/230.2; 544/71
(58) Field of Classification Search .................. 544/71; 514/230.2
See application file for complete search history.

(56) References Cited

U.S. PATENT DOCUMENTS

| 5,011,860 A | 4/1991 | Blythin et al. |
| 5,847,149 A | 12/1998 | Fuss et al. |
| 7,208,490 B2 | 4/2007 | Barbachyn et al. |

FOREIGN PATENT DOCUMENTS

| WO | WO 02/34753 | 5/2002 |
| WO | WO 03/091252 | 11/2003 |
| WO | WO2006120563 | 11/2006 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Snyder et al., J. Med. Liban 48(4): 208-214, 2000 (PubMed Abstract provided).*
Beke, Gyula, et al., "Syntheis and Stereochemistry of Dispiro Substituted Pyridazines: Application of Ellipticity-Absorbance Ratio Spectra for Providing Enantiomeric Relationship by HPLC-CD/UV Detection", Chirality, 2002, vol. 14, pp. 365-371.
Boehm, H.J., et al, J. Med. Chem., 2000, vol. 43, pp. 2664-2674.
Chen, D.K., et al, N. Engl. J. Med., 1999, vol. 341(4), pp. 233-239.
Chopra, I., et al, JAMA, 1996, vol. 275(5), pp. 401-403.
Csizmadia, Imre G., Journal of Molecular Structure (Theochem), 666, 2003, xii-xiv.
Database Chemicals Online, Chemical Abstracts Service, May 2003, XP002266425.
Declaration of Alexander R. Hurd, including Exhibits I and II.

D'Yachenko, E. V., et al., "tert-Amino effect in heterocyclic chemistry. Synthesis of hydrogenated spiro derivatives of quinolines", Russian Chemical Bulletin, International Edition, Jun. 2004, vol. 53, No. 6, pp. 1240-1247.
Gerlach, U., "Synthesis of Tricyclic Cyano-Substituted Tetrahydroquinolines by Radical Decyanation of Geminal Dinitriles", Tetrahedron Letters, 1995, vol. 36(29), pp. 5159-5162, XP004027630.
Gleave, D.L., et al, "Synthesis and Antibacterial activity of [6,5,5] and [6,6,5] Tricyclic Fused Oxazolidinones", Bioorganic & Medicinal Chemistry Letters, May 1998, vol. 8(10), pp. 1231-1236, XP004137053.
Glukhareva, T. V., et al., "Synthesis of Spiro Derivatives of Pyrrolo[1,2-a]Quinoline", Chemistry of Heterocyclic Compounds, 2002, vol. 38, No. 11, pp. 1426-1427.
Groenen, L.C., et al., "The tertiary amino effect in heterocyclic synthesis: Mechanistic and computational study of the formation of six-membered rings" Tetrahedron 1988, vol. 44(14), pp. 4637-4644.
Karolyhazy, Laszlo, et al., "Thermochemical study on the ring closure reaction of 5-morpholino-4-vinylpyridazinones by tert-amino effect", Journal of Molecular Structure (Theochem), 2003, 666-667, pp. 667-680
Kim, O.K., et al Exp. Opin. Ther. Patents, 1998, vol. 8(8), pp. 959-969.
Kotilainen, P., et al, J. Infect. Dis., 1990, vol. 161, pp. 41-44.
Maxwell, A., Trends in Microbiology, 1997, vol. 5(3), pp. 102-109.
Maxwell, A., Mol. Microbiol. 1993, vol. 9(4), 681-686.
Nijhuis, W.H.N., et al, "A Novel two-step Synthesis of Hexahydropyrazino [1'2-Alphau]-quinolines", Synthesis 1987, vol. 7, pp. 641-645, XP002266422.
Nijhuis, W.H.N., et al., "The tert-amino effect in heterocyclic chemistry: synthesis of tetra-and pentacyclic compounds" Recl. Trav. Chim. Pays-Bas 1989:108, 172-178.
Nijhuis, W.H.N., et al, "Stereochemical Aspects of the tert-Amino effect", J. Org. Chem., 1989, vol. 54(1), pp. 209-216, XP002266423.
Ojea, V., et al., "Synthesis of New Heterotricyclic Compounds Containing the [1,8]Naphthyridine Group by Thermal Isomerization of 2-Dialkylamino-3-vinylpyridines", Synthesis, 1991, pp. 798-802.
Ojea, V., et al., "Formation of New Heterotetracyclic Compounds by Ring Closure of 2-Amino-3-vinylpyridines", Synthesis, 1992, pp. 152-157.
Richards, H.C., "Oxamniquine: A Drug for the Tropics", in "The Role of Organic Chemistry in Drug Research", 1985, pp. 271-289.
Schwartz, A., et al., "Applications of tert-amino effect and a nitrone-olefin 1,3-dipolar cycloaddition reaction: synthesis of novel angularly annelated diazino heterocycles" Journal of Molecular Structure (Theochem) 2000, vol. 528, pp. 49-57.
Silver, L.L. and Bostian, A.K., Antimicrob. Agents and Chemother., Mar. 1993, vol. 37(3), pp. 377-383.

(Continued)

*Primary Examiner*—Kahsay T Habte
(74) *Attorney, Agent, or Firm*—B. Timothy Creagan; Gregg C. Benson

(57) ABSTRACT

Described herein are antibacterial compounds, methods for making the compounds, pharmaceutical compositions containing the compounds and methods of treating bacterial infections utilizing the compounds and pharmaceutical composition.

16 Claims, No Drawings

OTHER PUBLICATIONS

Tiwari, et al 5-Nitro-4(2)-[Oxo-3H-Quinazolin-3-yl]-benzyideue-mailonylureas as Antibacterial Agents, J. Indian Chem Soc, 1980, vol. 57/100, pp. 1039-1040.

Trucksis, M., et al, Ann. Intern. Med., 1991, vol. 114(5), pp. 424-426.

Verboom, Willem, et al. "tert-Amino effect in Heterocyclic Synthesis", Journal of Organic Chemistry, 1984, vol. 49(2), pp. 269-276, XP002266421.

CAS Registry No. 296244-43-4. Apr. 25, 2003. ChemDiv, Inc. Product Library.

CAS Registry No. 346630-58-8, No publication data provided, (Jun. 21, 2005).

CAS Registry No. 401608-21-7, May 18, 2005, Labo Test Stock.

CAS Registry No. 663946-83-6, Mar. 1, 2005, Compounds for Screening.

CAS Registry No. 695202-34-7, Jan. 1, 2004, Ambinter Stock Screening Collection.

CAS Registry No. 695211-58-6, Jan. 1, 2004, Ambinter Stock Screening Collection.

CAS Registry No. 695211-59-7, Jan. 1, 2004, Ambinter Stock Screening Collection.

CAS Registry No. 695220-71-4, Aug. 10, 2004, Chemical Block Stock Library.

CAS Registry No. 696630-59-6, Sep. 17, 2004, Interchim Intermediates.

CAS Registry No. 696658-91-0, Sep. 17, 2004, Interchim Intermediates.

CAS Registry No. 704678-02-4, Aug. 10, 2004, Chemical Block Stock Library.

CAS Registry No. 704878-08-0, Jun. 1, 2004, Tim Tec Oversees Stock.

CAS Registry No. 727370-63-0, Jun. 1, 2004, Tim Tec Oversees Stock.

CAS Registry No. 727371-95-1, Jun. 1, 2004, Tim Tec Oversees Stock.

CAS Registry No. 727671-74, Aug. 10, 2004, Chemical Block Stock Library.

CAS Registry No. 728036-02-0, Aug. 10, 2004, Chemical Block Stock Library.

* cited by examiner

ANTIBACTERIAL AGENTS

CROSS-REFERENCE TO RELATED APPLICATIONS

This application claims the benefit of priority of U.S. provisional application No. 60/753,262 filed on Dec. 22, 2005, under 35 U.S.C. § 119(e)(i), which is incorporate herein by referenced in its entirety.

FIELD OF THE INVENTION

Described herein are antibacterial compounds, their use as antibacterial agents, pharmaceutical compositions containing these compounds, and methods for their preparation.

BACKGROUND OF THE INVENTION

Antibacterial resistance is a global clinical and public health problem that has emerged with alarming rapidity in recent years and undoubtedly will increase in the near future. Resistance is a problem in the community as well as in health care settings, where transmission of bacteria is greatly amplified. Because multiple drug resistance is a growing problem, physicians are now confronted with infections for which there is no effective therapy. The morbidity, mortality, and financial costs of such infections pose an increasing burden for health care systems worldwide. Strategies to address these issues emphasize enhanced surveillance of drug resistance, increased monitoring and improved usage of antimicrobial drugs, professional and public education, development of new drugs, and assessment of alternative therapeutic modalities.

As a result, alternative and improved agents are needed for the treatment of bacterial infections, particularly for the treatment of infections caused by resistant strains of bacteria, e.g. penicillin-resistant, methicillin-resistant, ciprofloxacin-resistant, and/or vancomycin-resistant strains.

SUMMARY OF THE INVENTION

One embodiment provides a compound having formula I:

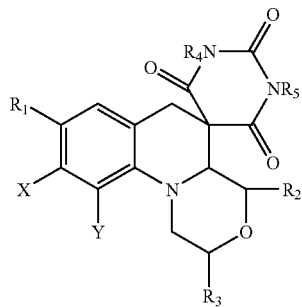

or a salt, solvate, hydrate or prodrug thereof.

In the above formula, $R_1$ is a substituted or unsubstituted pyrazine;

$R_2$ and $R_3$ are independently H or substituted or unsubstituted $C_{1-6}$ alkyl;

$R_4$ and $R_5$ are independently H, a substituted or unsubstituted $C_{1-6}$ alkyl, a substituted or unsubstituted ether, substituted or unsubstituted —$(CH_2)_m$aryl, substituted or unsubstituted —O$(CH_2)_m$aryl, —$(CH_2)_m NR_8R_9$, —$(CH_2)_m OR_6$, —$(CH_2)_m OPO_3(R_p)_2$, —$(CH_2)_m OC(=O)(CH_2)_m CH_3$, —$(CH_2)_m OC(=O)(CH_2)_m CO_2R_6$, —$(CH_2)_m OC(=O)(CH_2)_m NR_8R_9$, —$(CH_2)_m OC(=O)E$ or $R_4$ and $R_5$ together with the atoms to which they are attached form a substituted or unsubstituted heterocyclic ring;

each m is independently 0, 1, 2 or 3;

E is a substituted or unsubstituted ether;

each $R_p$ is independently H, $C_{1-6}$ alkyl, benzyl, substituted benzyl, phenyl, substituted phenyl, or $(R_p)_2$ together with the atoms to which they are attached form a substituted or unsubstituted heterocyclic ring;

each $R_6$ is independently H, substituted or unsubstituted $C_{1-6}$ alkyl, $C_{1-6}$ acyl or benzyl;

$R_8$ and $R_9$ are independently H, substituted or unsubstituted $C_{1-6}$ alkyl or $R_8$ and $R_9$ together with the atom to which they are attached form a substituted or unsubstituted heterocyclic ring; and X and Y are independently H, halo, substituted or unsubstituted $C_{1-6}$ alkyl, —$OR_6$, —CN, a substituted or unsubstituted ether, a substituted or unsubstituted heterocyclyl, or a substituted or unsubstituted amine.

Forms of the compounds can include salts, such as pharmaceutically acceptable salts, solvates, hydrates or prodrugs of the described compounds. The described compounds can also be part of a pharmaceutical composition, which can additionally include a pharmaceutically acceptable carrier, diluent or excipient.

Such compounds and compositions exhibit antibacterial activity and can be used accordingly.

DETAILED DESCRIPTION

Provided herein are compounds of Formula I. When describing the compounds of Formula I, for example when naming the compounds, the ring system is numbered as follows:

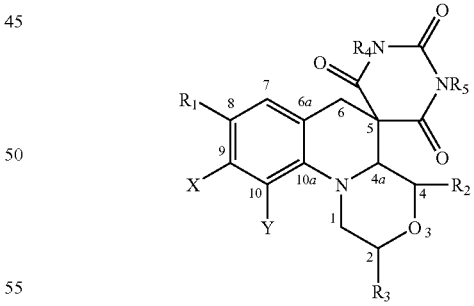

In some compounds, $R_1$ is:

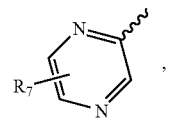

for example

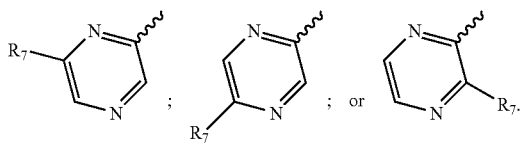

In these embodiments, ∿∿∿ indicates a point of attachment and the pyrazine can be substituted with one, two, three or more $R_7$ groups;

$R_7$ is H, halo, substituted or unsubstituted $C_{1-6}$ alkyl, substituted or unsubstituted $C_3$-$C_8$ cycloalkyl, substituted or unsubstituted heterocyclyl, a substituted or unsubstituted ether, —CN —$(CH_2)_mOPO_3(R_p)_2$, —$(CH_2)_mOC(=O)(CH_2)_mCH_3$, —$(CH_2)_mOC(=O)(CH_2)_mCO_2R_6$, —$(CH_2)_mOC(=O)(CH_2)_mNR_8R_9$, —$(CH_2)_mOC(=O)E$, —$(CH_2)_mCO_2(CH_2)_mCH_3$, —$(CH_2)_mCO_2(CH_2)_mCO_2R_6$, —$(CH_2)_mCO_2(CH_2)_mNR_8R_9$, —$(CH_2)_mCO_2E$, —$(CH_2)_mC(=O)NR_6(CH_2)_mCO_2R_6$, —$(CH_2)_mC(=O)NR_8R_9$, —$(CH_2)_mNR_8R_9$, —$(CH_2)_mPO_3(R_{11})_2$, —$(CH_2)_mOR_{10}$, which is optionally substituted with —$OR_{11}$, —$(CH_2)_mC(=O)OR_{11}$, —$(CH_2)_mNR_{11}SO_nR_{12}$, —$(CH_2)_mSO_nR_{12}$, —$(CH_2)_mSO_nNR_8R_9$, substituted or unsubstituted aryl, or substituted or unsubstituted heteroaryl;

each m is as above, each n is independently 0, 1 or 2;

$R_{10}$ is H, substituted or unsubstituted $C_{1-6}$ alkyl, —$PO_3H_2$, $C(=O)R_{13}$, $C(=O)OR_{13}$ or $C(=O)NR_8R_9$; and $R_{11}$, $R_{12}$ and $R_{13}$ are independently H, substituted or unsubstituted $C_{1-6}$ alkyl, substituted or unsubstituted aminoalkyl, an amino acid residue or a peptide residue. Examples of amino acid residues include alanine, aspartic acid, glycine, glutamic acid, histidine, lysine or valine.

In some instances, a nitrogen of the pyrazine ring can be substituted, for example with an oxygen in

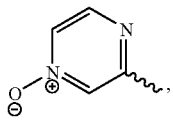

which can also be depicted as

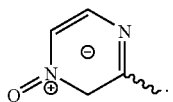

In certain compounds, X is H, Y is H or both X and Y are H. In other compounds X is F, Y is F or both X and Y are F. In these and other compounds, $R_2$ and $R_3$ can be methyl. In some compounds X can be substituted or unsubstituted —$OR_6$, and in some instances $R_6$ can be ethyl. Alternatively, X can be a substituted or unsubstituted ether or an amine.

In some embodiments, X, Y or both can be a substituted or unsubstituted ether. In the compounds, none, one or both of $R_4$ and $R_5$ can be H. $R_4$ and $R_5$ can also independently be ethers.

Alternatively, independently X, Y or both can be a substituted or unsubstituted amine. When X or Y is a substituted or unsubstituted amine, then the group can independently have the formula —$(CH_2)_mNR_8R_9$ and each m, $R_8$ and $R_9$ is independent of any other m, $R_8$ and $R_9$ values at other positions. When any $R_8$ and $R_9$ together with the atom to which they are attached form a substituted or unsubstituted heterocyclic ring, the ring can be a monocyclic ring system, for example containing three to eight ring atoms, or the ring system can be a bi- or polyheterocyclic ring system. Additionally, one or more ring atoms, in addition to the N to which $R_8$ and $R_9$ are attached, can be selected from non-carbon atoms, for example N, O or S.

In some embodiments $R_4$ and $R_5$ are the same, for example where both are H. $R_4$ or $R_5$ can also be substituted or unsubstituted —$(CH_2)_m$aryl or —$O(CH_2)_m$aryl, such as substituted or unsubstituted benzyl or substituted or unsubstituted —Obenzyl.

In certain compounds, when $R_8$ and $R_9$ together with the atom to which they are attached form a substituted or unsubstituted heterocyclic ring, the heterocyclic ring can have three, four, five, six, seven, eight or more ring members and include one, two, three or more heteroatoms, such as N, O or S. Specific examples of such heterocyclic rings include morpholine and piperazine or a substituted piperazine.

In certain embodiments, $R_{11}$, $R_{12}$ or $R_{13}$ can be an amino acid residue. Amino acid residues are molecules that contain both amino and carboxylic acid functional groups. Some amino acids can be represented by the formula —$C(=O)CH(Z)NHR_a$, where Z alone can be a side chain of a naturally or non-naturally occurring amino acid. In cyclic amino acids, such as proline, Z in combination with $R_a$ can be a side chain of a naturally or non-naturally occurring amino acid. When $R_a$ is not part of the amino acid side chain, then generally $R_a$ is H. Amino acids and peptides can be C- or N-linked. Examples of amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. Other amino acids include gamma-aminobutyric acid (GABA), carnitine, ornithine, citrulline, homocysteine, hydroxyproline, hydroxylysine, and sarcosine. The amino acids can be in the L- or D-configuration.

Alternatively, $R_{11}$, $R_{12}$ or $R_{13}$ can be a peptide residue, which can be C- or N-linked. Peptides are amino acids linked together via peptide bonds and can be straight-chained or branched. Suitable peptides can include dipeptides, tripeptides, tetrapeptides or more in which the amino acid residues making up the peptide can be the same or different.

In some embodiments, $(R_p)_2$ together with the atoms to which they are attached form a substituted or unsubstituted heterocyclic ring. In some compounds the oxygen atoms can be connected via an alkyl, aryl, or alkyl-aryl-alkyl bridge, such as in

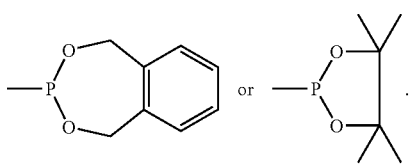

In some of the compounds each E or ether independently has the formula —$[(CV_2)_pO(CV_2)_p]_qCH_3$ wherein each p is independently 0, 1, 2, 3, 4, 5 or 6, each q is independently 1, 2, 3, 4, 5 or 6, each V is independently H or another —$[(CV_2)_pO(CV_2)_p]_qCH_3$. Examples of these compounds include where each E or ether independently has the formula —[(CH$_2$)$_p$O(CH$_2$)$_p$]$_q$CH$_3$ where each p is independently 0, 1, 2, 3 or 4 and each q is independently 1, 2, 3 or 4.

In some specific embodiments, X and Y are F, R$_2$ and R$_3$ are methyl, and R$_4$ and R$_5$ are H. In additional specific embodiments, X is F, Y is H, R$_2$ and R$_3$ are methyl, and R$_4$ and R$_5$ are H. In further specific embodiments, X is H, Y is F, R$_2$ and R$_3$ are methyl, and R$_4$ and R$_5$ are H. In some specific embodiments, X and Y are H, R$_2$ and R$_3$ are methyl, and R$_4$ and R$_5$ are H. In further specific embodiments, X and Y are F, R$_2$ and R$_3$ are methyl, and R$_4$ and R$_5$ are a substituted or unsubstituted ether, —(CH$_2$)$_m$NR$_8$R$_9$, —(CH$_2$)$_m$OR$_6$, —(CH$_2$)$_m$OPO$_3$(R$_p$)$_2$, —(CH$_2$)$_m$OC(=O)(CH$_2$)$_m$CH$_3$, —(CH$_2$)$_m$OC(=O)(CH$_2$)$_m$CO$_2$R$_6$, —(CH$_2$)$_m$OC(=O)(CH$_2$)$_m$NR$_8$R$_9$, or —(CH$_2$)$_m$OC(=O)E. In certain of these embodiments, m is 1 or 2. In other specific embodiments, X is F, Y is H, R$_2$ and R$_3$ are methyl, and R$_4$ and R$_5$ are a substituted or unsubstituted ether, —(CH$_2$)$_m$NR$_8$R$_9$, —(CH$_2$)$_m$OR$_6$, —(CH$_2$)$_m$OPO$_3$(R$_p$)$_2$, —(CH$_2$)$_m$OC(=O)(CH$_2$)$_m$CH$_3$, —(CH$_2$)$_m$OC(=O)(CH$_2$)$_m$CO$_2$R$_6$, —(CH$_2$)$_m$OC(=O)(CH$_2$)$_m$NR$_8$R$_9$, or —(CH$_2$)$_m$OC(=O)E. In certain of these embodiments, m is 1 or 2. In some of these compounds R$_7$ can be H, C$_{1-6}$ alkyl, such as a methyl, —NR$_8$R$_9$ or —OR$_{10}$. In other embodiments, R$_7$ is a substituted or unsubstituted ether, —(CH$_2$)$_m$OPO$_3$(R$_p$)$_2$, —(CH$_2$)$_m$OC(=O)(CH$_2$)$_m$CH$_3$, —(CH$_2$)$_m$OC(=O)(CH$_2$)$_m$CO$_2$R$_6$, —(CH$_2$)$_m$OC(=O)(CH$_2$)$_m$NR$_8$R$_9$, —(CH$_2$)$_m$OC(=O)E, —(CH$_2$)$_m$CO$_2$(CH$_2$)$_m$CH$_3$, —(CH$_2$)$_m$CO$_2$(CH$_2$)$_m$CO$_2$R$_6$, —(CH$_2$)$_m$CO$_2$(CH$_2$)$_m$NR$_8$R$_9$, —(CH$_2$)$_m$CO$_2$E, —(CH$_2$)$_m$C(=O)NR$_6$(CH$_2$)$_m$CO$_2$R$_6$, —(CH$_2$)$_m$C(=O)NR$_8$R$_9$, —(CH$_2$)$_m$NR$_8$R$_9$, —(CH$_2$)$_m$PO$_3$(R$_{11}$)$_2$, —(CH$_2$)$_m$C(=O)OR$_{11}$, —(CH$_2$)$_m$NR$_{11}$SO$_n$R$_{12}$, —(CH$_2$)$_m$SO$_n$R$_{12}$, or —(CH$_2$)$_m$SO$_n$NR$_8$R$_9$. In certain of these embodiments, m is 1 or 2.

In a subset of the compounds of Formula I, the compounds can have the stereochemistry shown in Formula Ib below:

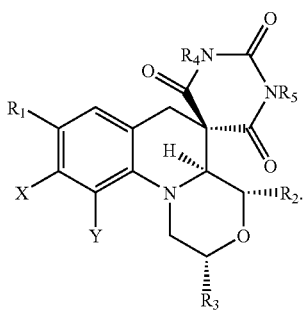

Any embodiment described herein can be combined with any other suitable embodiment described herein to provide additional embodiments. For example, where one embodiment individually or collectively describes possible groups for R$_1$, R$_2$, R$_3$, R$_4$, R$_5$, etc., and a separate embodiment describes possible R$_7$ groups, it is understood that these embodiments can be combined to provide an embodiment describing possible groups for R$_1$, R$_2$, R$_3$, R$_4$, R$_5$, etc. with the possible R$_7$ groups, etc. With respect to the above compounds, and throughout the application and claims, the following terms have the meanings defined below.

The phrase "acyl" refers to groups having a carbon double-bonded to an oxygen atom, such as in the structure —C(=O)R. Examples of R can include H, such as in aldehydes, a hydrocarbon, such as in a ketone, —NR$_8$R$_9$, such as in an amide, —OR$_6$ such as in a carboxylic acid or ester, —OOCR$_2$, such as in an acyl anhydride or a halo, such as in an acyl halide.

The phrase "alkenyl" refers to straight and branched chain hydrocarbons, such as those described with respect to alkyl groups described herein, that include at least one double bond existing between two carbon atoms. Examples include vinyl, —CH=C(H)(CH$_3$), —CH=C(CH$_3$)$_2$, —C(CH$_3$)=C(H)$_2$, —C(CH$_3$)=C(H)(CH$_3$), —C(CH$_2$CH$_3$)=CH$_2$, cyclohexenyl, cyclopentenyl, cyclohexadienyl, butadienyl, pentadienyl, and hexadienyl among others. An alkenyl group can optionally be substituted, for example where 1, 2, 3, 4, 5, 6, 7, 8 or more hydrogen atoms are replaced by a substituent selected from the group consisting of halogen, haloalkyl, hydroxy, thiol, cyano, and —NR$_8$R$_9$.

The phrase "alkyl" refers to hydrocarbon chains, for example C$_{1-6}$ chains, that do not contain heteroatoms. Thus, the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase includes primary alkyl groups, secondary alkyl groups, and tertiary alkyl groups. Alkyl groups can be bonded to one or more carbon atom(s), oxygen atom(s), nitrogen atom(s), and/or sulfur atom(s) in the parent compound. An alkyl group can optionally be substituted, for example where 1, 2, 3, 4, 5, 6 or more hydrogen atoms are replaced by a substituent selected from the group consisting of halogen, haloalkyl, hydroxy, thiol, cyano, and —NR$_8$R$_9$.

The phrase "alkylene" refers to a straight or branched chain divalent hydrocarbon radical, generally having from two to ten carbon atoms.

The phrase "alkynyl" refers to straight and branched chain hydrocarbon groups, such as those described with respect to alkyl groups as described herein, except that at least one triple bond exists between two carbon atoms. Examples include —C≡C(H), —C≡C(CH$_3$), —C≡C(CH$_2$CH$_3$), —C(H$_2$)C≡C(H), —C(H)$_2$C≡C(CH$_3$), and —C(H)$_2$C≡C(CH$_2$CH$_3$) among others. An alkynyl group can optionally be substituted, for example where 1, 2, 3, 4, 5, 6, 7, 8 or more hydrogen atoms are replaced by a substituent selected from the group consisting of halogen, haloalkyl, hydroxy, thiol, cyano, and —NR$_8$R$_9$.

The phrase "aminoalkyl" refers to an alkyl group as above attached to an amino group, which can ultimately be a primary, secondary or tertiary amino group. An example of an amino alkyl group is the —NR$_8$R$_9$ where one or both of R$_8$ and R$_9$ is a substituted or unsubstituted C$_{1-6}$ alkyl or R$_8$ and R$_9$ together with the atom to which they are attached form a substituted or unsubstituted heterocyclic ring. Specific aminoalkyl groups include —NHCH$_3$, —N(CH$_3$)$_2$, —NHCH$_2$CH$_3$, —N(CH$_3$)CH$_2$CH$_3$, —N(CH$_2$CH$_3$)$_2$, —NHCH$_2$CH$_2$CH$_3$, —N(CH$_2$CH$_2$CH$_3$)$_2$, and the like. Additional aminoalkyl groups include:

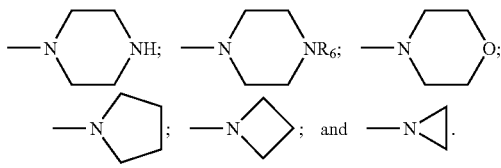

An aminoalkyl group can optionally be substituted with 1, 2, 3, 4 or more non-hydrogen substituents, for example where each substituent is independently selected from the group consisting of halogen, cyano, hydroxy, C$_{1-6}$ alkyl, C$_{1-6}$ alkoxy, C$_{1-2}$ alkyl substituted with one or more halogens, C$_{1-2}$ alkoxy substituted with one or more halogens, —C(O)R$_6$, —C(O)OR$_6$, —S(O)$_n$R$_6$ and —NR$_8$R$_9$. These substituents may be the same or different and may be located at any position of the ring that is chemically permissible.

The phrase "aryl" refers to cyclic or polycyclic aromatic rings, generally having from 5 to 12 carbon atoms. Thus the phrase includes, but is not limited to, groups such as phenyl, biphenyl, anthracenyl, naphthenyl by way of example. The phrase "unsubstituted aryl" includes groups containing condensed rings such as naphthalene. Unsubstituted aryl groups can be bonded to one or more carbon atom(s), oxygen atom(s), nitrogen atom(s), and/or sulfur atom(s) in the parent compound. Substituted aryl groups include methoxyphenyl groups, such as para-methoxyphenyl.

Substituted aryl groups include aryl groups in which one or more aromatic carbons of the aryl group is bonded to a substituted and/or unsubstituted alkyl, alkenyl, alkynyl group or a heteroatom containing group as described herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, and hydroxyphenyl among others. An aryl moiety can optionally be substituted with 1, 2, 3, 4 or more non-hydrogen substituents, for example where each substituent is independently selected from the group consisting of halogen, cyano, hydroxy, C$_{1-6}$ alkyl, C$_{1-6}$ alkoxy, C$_{1-2}$ alkyl substituted with one or more halogens, C$_{1-2}$ alkoxy substituted with one or more halogens, —C(O)R$_6$, —C(O)OR$_6$, —S(O)$_n$R$_6$ and —NR$_8$R$_9$. These substituents may be the same or different and may be located at any position of the ring that is chemically permissible.

The phrase "cycloalkyl" refers to cyclic hydrocarbon chains, generally having from 3 to 12 carbon atoms, and includes cyclic alkyl groups such as cyclopropyl, cyclobutyl, cyclopentyl, cyclohexyl, cycloheptyl, and cyclooctyl and such rings substituted with straight and branched chain alkyl groups as described herein. The phrase also includes polycyclic alkyl groups such as, but not limited to, adamantly, norbornyl, and bicyclo[2.2.2]octyl and such rings substituted with straight and branched chain alkyl groups as described herein. Cycloalkyl groups can be saturated or unsaturated and can be bonded to one or more carbon atom(s), oxygen atom(s), nitrogen atom(s), and/or sulfur atom(s) in the parent compound. A cycloalkyl group can be optionally substituted, for example where 1, 2, 3, 4 or more hydrogen atoms are replaced by a substituent selected from the group consisting of halogen, cyano, hydroxy, C$_{1-6}$ alkyl, C$_{1-6}$ alkoxy, C$_{1-2}$ alkyl substituted with one or more halogens, C$_{1-2}$ alkoxy substituted with one or more halogens, —C(O)R$_6$, —C(O)OR$_6$, —S(O)$_n$R$_6$ and —NR$_8$R$_9$.

Ethers, as used herein, generically encompass monoethers, polyethers, straight chain ethers, branched ethers and cyclic ethers. Straight chain ethers can have the structure —[(CH$_2$)$_p$O(CH$_2$)$_p$]$_q$CH$_3$ where each p is independently 0, 1, 2, 3, 4, 5 or 6 and q is 1, 2, 3, 4, 5 or 6. Branched ethers can have the formula —[(CV$_2$)$_p$O(CV$_2$)$_p$]$_q$CH$_3$ where each V is independently H or another —[(CV$_2$)$_p$O(CV$_2$)$_p$]$_q$CH$_3$ group. Cyclic ethers can have the formula

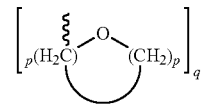

where p and q are as above and $\sim\!\!\sim\!\!\sim$ indicates a point of attachment. Specifically, as ether compounds, there are -dimethyl ether, -methyl ethyl ether, -methoxy ethyl ether, -diethyl ether, -methyl t-butyl ether, -methyl cellosolve, -ethylene glycol dimethyl ether, -diethylene glycol dimethyl ether, -triethylene glycol dimethyl ether, -tetraethylene glycol dimethyl ether, -tetrahydrofuran, -1,4-dioxane, and the like.

The phrase "halo" refers to fluorine, chlorine, bromine or iodine.

The phrase "haloalkyl" refers to an alkyl group in which at least one, for example 1, 2, 3, 4, 5 or more, hydrogen atom(s) is/are replaced with a halogen. Examples of suitable haloalkyls include chloromethyl, difluoromethyl, trifluoromethyl, 1-fluro-2-chloro-ethyl, 5-fluoro-hexyl, 3-difluro-isopropyl, 3-chloro-isobutyl, etc.

The phrases "heterocyclyl" or "heterocyclic ring" refers to aromatic, nonaromatic, saturated and unsaturated ring compounds including monocyclic, bicyclic, and polycyclic ring compounds, including fused, bridged, or spiro systems, such as, but not limited to, quinuclidyl, containing 1, 2, 3 or more ring members of which one or more is a heteroatom such as, but not limited to, N, O, P and S. Unsubstituted heterocyclyl groups include condensed heterocyclic rings such as benzimidazolyl. Examples of heterocyclyl groups include: unsaturated 3 to 8 membered rings containing 1 to 4 nitrogen atoms such as, but not limited to pyrrolyl, pyrrolinyl, imidazolyl, imidazolidinyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3 to 8 membered rings containing 1 to 4 nitrogen atoms such as, but not limited to, pyrrolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; saturated 3 to 8 membered rings containing 1 to 3 oxygen atoms such as, but not limited to, tetrahydrofuran; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3, 4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as; but not limited to, dihydrooxathiinyl; saturated 3 to 8 membered rings containing 1 to 2 oxygen atoms, and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl groups also include those described herein in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Heterocyclyl groups can contain 5 or 6 ring members. Examples of heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

A heterocyclyl group can be optionally substituted, for example where 1, 2, 3, 4 or more hydrogen atoms are replaced by a substituent selected from the group consisting of halogen, cyano, hydroxy, $C_{1-6}$ alkyl, $C_{1-6}$ alkoxy, $C_{1-2}$ alkyl substituted with one or more halogens, $C_{1-2}$ alkoxy substituted with one or more halogens, —C(O)R$_6$, —C(O)OR$_6$, —S(O)$_n$R$_6$ and —NR$_8$R$_9$. Examples of "substituted heterocyclyl" rings include 2-methylbenzimidazolyl, 5-methylbenzimidazolyl, 5-chlorobenzthiazolyl, 1-methylpiperazinyl, and 2-chloropyridyl among others. Any nitrogen atom within a heterocyclic ring can optionally be substituted with $C_{1-6}$ alkyl, if chemically permissible.

Heterocyclyl groups include heteroaryl groups as a subgroup. The phrase "heteroaryl" refers to a monovalent aromatic ring radical, generally having 5 to 10 ring atoms, containing 1, 2, 3, or more heteroatoms independently selected from S, O, or N. The term heteroaryl also includes bicyclic groups in which the heteroaryl ring is fused to a benzene ring, heterocyclic ring, a cycloalkyl ring, or another heteroaryl ring. Examples of heteroaryl include 7-benzimidazolyl, benzo[b]thienyl, benzofuryl, benzothiazolyl, benzothiophenyl, 2-, 4-, 5-, 6-, or 7-benzoxazolyl, furanyl, furyl, imidazolyl, indolyl, indazolyl, isoquinolinyl, isothiazolyl, isoxazolyl, oxadiazolyl, oxazolyl, purinyl, pyrazinyl, pyrazolyl, pyridazinyl, pyridinyl, pyrimidinyl, pyrrolyl, quinolinyl, tetrazolyl, thiadiazolyl, thiazolyl, thienyl, thiophenyl, triazolyl and the like. Heteroaryl rings can also be optionally fused to one or more of another heterocyclic ring(s), heteroaryl ring(s), aryl ring(s), cycloalkenyl ring(s), or cycloalkyl rings. A heteroaryl group can be optionally substituted, for example where 1, 2, 3, 4 or more hydrogen atoms are replaced by a substituent selected from the group consisting of halogen, cyano, hydroxy, $C_{1-6}$ alkyl, $C_{1-6}$ alkoxy, $C_{1-2}$ alkyl substituted with one or more halogens, $C_{1-2}$ alkoxy substituted with one or more halogens, —C(O)R$_6$, —C(O)OR$_6$, —S(O)$_n$R$_6$ and —NR$_8$R$_9$.

The phrase "heterocyclyloxy" refers to a group in which an oxygen atom is bound to a ring atom of a heterocyclyl group as described herein.

"Pharmaceutically acceptable" means suitable for use in mammals. A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid. Examples of pharmaceutically acceptable salts are described in Berge, S. M. et al., "Pharmaceutical Salts," Journal of Pharmaceutical Science, 1977;66:1 19.

A "prodrug" is a compound that can be transformed in vivo into an active therapeutic compound, such as a compound described herein. Transformation of the prodrug compound can be accomplished chemically, enzymatically, or by action with other endogenous materials, e.g. amino acids, peptides and proteins. Prodrugs are discussed in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987. Examples of prodrugs can include esters and amides of polar groups, such as carboxylate groups.

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include amides such as, formamide, acetamide, trifluoroacetamide, and benzamide; imides, such as phthalimide, and dithiosuccinimide; and others. Examples of protected sulfhydryl groups include thioethers such as S-benzyl thioether, and S-4-picolyl thioether; substituted S-methyl derivatives such as hemithio, dithio and aminothio acetals; and others.

A "salt" refers to all salt forms of a compound, including salts suitable for use in industrial processes, such as the preparation of the compound, and pharmaceutically acceptable salts.

"Substituted" refers to a group in which one or more bonds to a hydrogen atom contained therein are replaced by a bond to non-hydrogen atom. In some instances the bond will also be replaced by non-carbon atoms such as, but not limited to: a halogen atom such as F, Cl, Br, and I; a nitrogen atom in groups such as amines, amides, alkylamines, dialkylamines, arylamines, alkylarylamines, diarylamines, heterocyclylamine, (alkyl)(heterocyclyl)amine, (aryl)(heterocyclyl)amine, or diheterocyclylamine groups, isonitrile, N-oxides, imides, and enamines; an oxygen atom in groups such as hydroxyl groups, alkoxy groups, aryloxy groups, ester groups, and heterocyclyloxy groups; a silicon atom in groups such as in trialkylsilyl groups, dialkylarylsilyl groups, alkyldiarylsilyl groups, and triarylsilyl groups; a sulfur atom in groups such as thiol groups, alkyl and aryl sulfide groups, sulfone groups, sulfonyl groups, and sulfoxide groups; and other heteroatoms in various other groups. Substituted alkyl groups and substituted cycloalkyl groups also include groups in which one or more bonds to one or more carbon or hydrogen atoms are replaced by a bond to a heteroatom such as oxygen in carbonyl, carboxyl, and ether groups; nitrogen in groups such as imines, oximes and hydrazones. Substituted cycloalkyl, substituted aryl, substituted heterocyclyl and substituted heteroaryl also include rings and fused ring systems which can be substituted with alkyl groups as described herein. Substituted arylalkyl groups can be substituted on the aryl group, on the alkyl group, or on both the aryl and alkyl groups. All groups included herein, such as alkyl, alkenyl, alkylene, alkynyl, aryl, heterocyclyl, heterocyclyloxy, and the like, can be substituted. Representative examples of substituents for substitution include one or more, for example one, two or three, groups independently selected from halogen, —OH, —$C_{1-6}$ alkyl, $C_{1-6}$ alkoxy, trifluoromethoxy, —$S(O)_n$ $C_{1-6}$ alkyl, amino, haloalkyl, thiol, cyano, —$OR_{10}$ and —$NR_8R_9$, and trifluoromethyl.

"Treating" means an alleviation of symptoms associated with an infection, halt of further progression or worsening of those symptoms, or prevention or prophylaxis of the infection. Treatment can also include administering the pharmaceutical formulations of the present invention in combination with other therapies. For example, the compounds and pharmaceutical formulations of the present invention can be administered before, during, or after surgical procedure and/or radiation therapy. The compounds of the invention can also be administered in conjunction with other antibacterial drugs.

In some instances, compounds described herein can be provided ex vivo or produced in vivo, for example where a prodrug of a compound is administered.

Generally, reference to a certain element such as hydrogen or H is meant to include all isotopes of that element. For example, if an R group is defined to include hydrogen or H, it also includes deuterium and tritium. Chemical formulas throughout are designated with capital Roman numerals for simplified identification. Roman numerals used in conjunction with a small letter, for example Ia, indicate that the structure set forth is an enantiomer of the compound identified by the Roman numeral. Roman numerals used in conjunction with a prime symbol, for example III', indicate that the structure set forth can have one or more protected groups which are included in atoms groups identified with the prime symbol, for example where O' indicates an oxygen atom or a protected aldehyde group.

General Synthesis of Compounds. The described compounds can be made according to the following general synthetic schemes, in which all R, X and Y have the values described above, B' is a is boronic acid or a boronate ester, such as

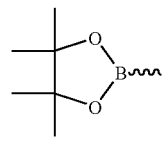

and O' is oxygen, giving an aldehyde, or a protected aldehyde group.

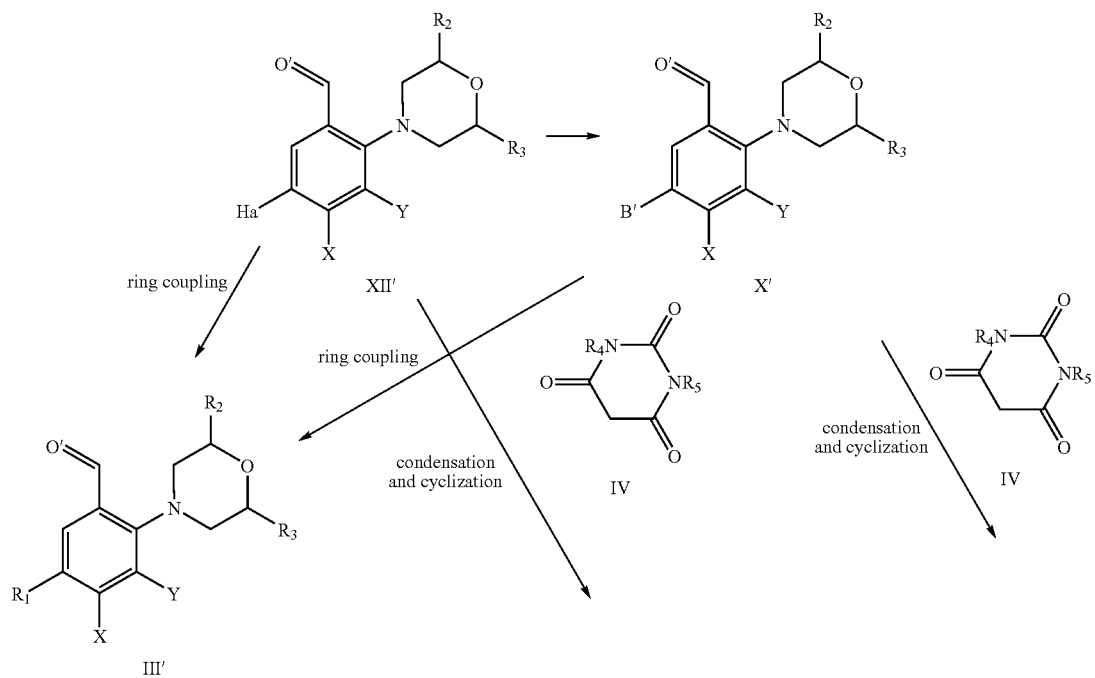

-continued

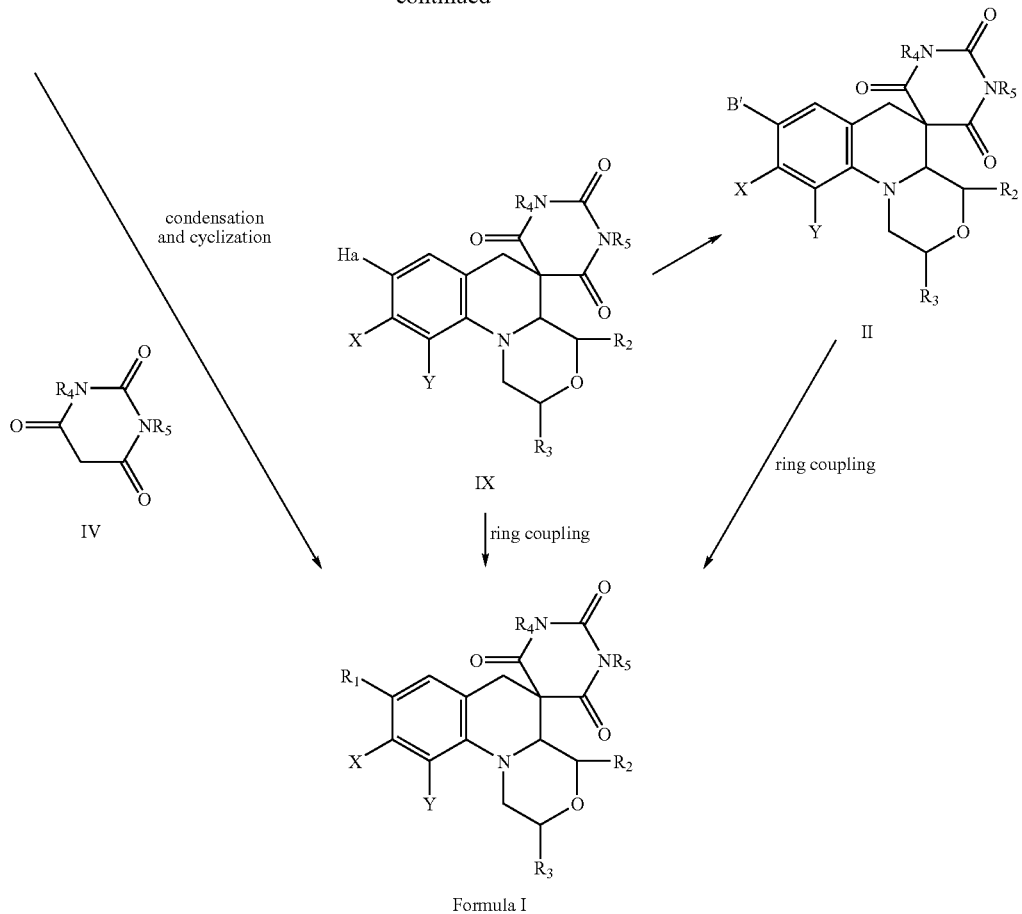

Formula I

In some cases it may be necessary to protect the aldehyde prior to performing a coupling reaction, such as the conversions of XII' to III', X' to III' or XII' to X'. In these instances, the aldehyde may be protected for example as an acetal by reaction with a diol such as ethylene diol, propane-1,3-diol or 2,2-dimethylpropane-1,3-diol. More specifically, the aldehyde may be reacted with a diol in a non-polar solvent by warming to 60-140° C. for 2 to 24 hours in the presence of a catalytic amount of protic acid such as para-toluenesulfonic acid or pyridinium para-toluene sulfonate. Alternative methods of masking the aldehyde, including alternative protecting groups or reduction to the corresponding alcohol and protection of the alcohol will be known to one skilled in the art.

In one embodiment, a substituted or unsubstituted pyrazine ring having an attached boron group, such as B', is coupled with compound XII', for example via an organometallic cross-coupling reaction, to give the compound of formula III'. The compound of formula I can be obtained from compound III' by condensation with a compound of formula IV, such as barbituric acid, and cyclization. Alternatively, compound IX can be obtained by condensation of compounds IV and XII' and cyclization. The compound of formula I can be obtained from compound IX by coupling a substituted or unsubstituted pyrazine ring having an attached boron group, for example via an organometallic cross-coupling reaction. In this scheme, formation of compound X' from compound XII or compound III' from compound X' may require the use of a protected aldehyde. In the above, reaction, Ha is hydrogen or a halogen, for example bromine. Ha can also be chlorine or iodine.

In another embodiment, compound X', containing a B' group, is coupled to a substituted or unsubstituted pyrazine ring having an attached halogen, to give the compound of formula III'. Alternatively, compound X' can be converted to compound II by condensation with a compound of formula IV, such as barbituric acid, and cyclization. Compound II can also be obtained from compound IX by substituting the halogen with a B' group by reaction with a borane as described herein. The compound of formula I can be made from compound II by coupling a substituted or unsubstituted pyrazine ring as described herein. In some embodiments, compound X' can be made from compound XII' by substituting the halogen with a B' group by reaction with a borane as described herein. Accordingly, the cross-coupling reaction may be performed either before condensation with compound IV and cyclization, or subsequent to introduction of compound IV.

When introduction of the pyrazine ring by cross-coupling is performed subsequent to introduction of the compound IV, in some cases it is desirable to protect the amide groups in the compound, particularly when $R_4$ and $R_5$ are H. The protecting group may take the form of a transient group that is removed after the cross-coupling reaction, or it may be a prodrug moiety that is retained or further modified for use in modulating the potency and/or delivery of the compound. An illustration of this protection scheme is shown below.

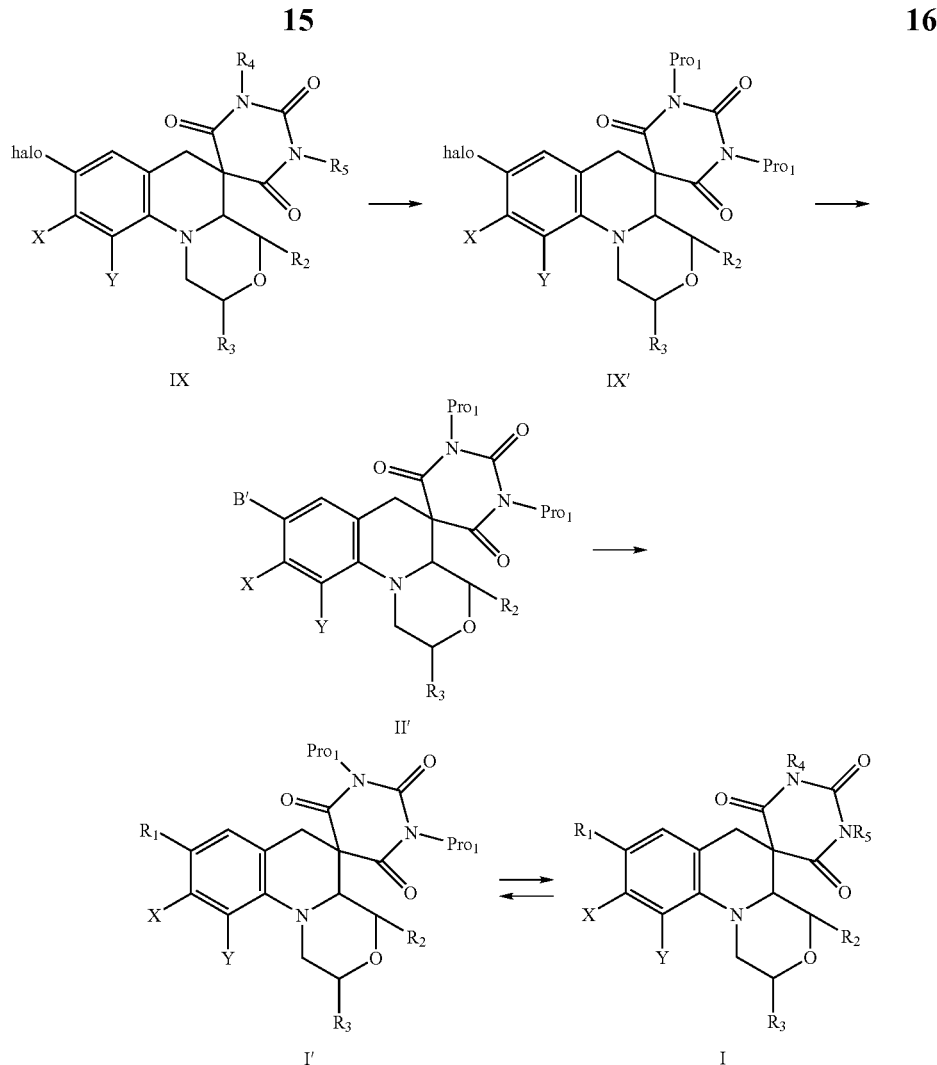

Also provided is a method for making the compounds of formula Ia shown below. This method can be performed by (a) reacting a compound of formula IIIa with a compound of formula IV at a temperature sufficient to produce a compound of formula Ia:

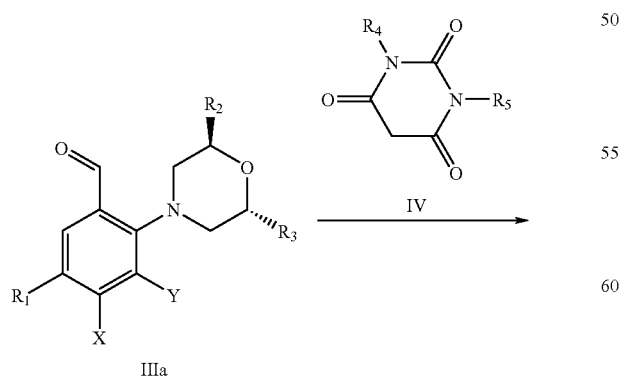

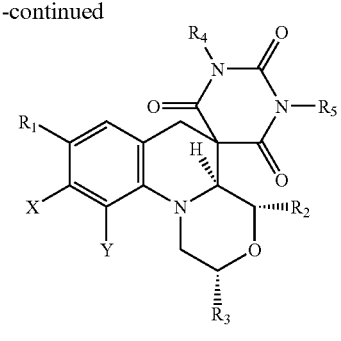

According to this method, specific groups can be defined as elsewhere herein. Reaction to form Ia can occur in an aqueous or organic solvent. Typically temperatures for this reaction will be about 60 to about 180° C., for example from about 80 to 100° C., 100 to 140° C. or 140 to 180° C., and can occur from about 0.5 to about 24 hours, for example 0.5, 1, 1.5, 2, 4, 6, 8, 10, 12, 14, 16, 18, 20, 22 or 24 hours. Examples of solvents that can be used include acetic acid, glacial or mixed with water, DMSO, methanol, isopropanol, butanol, toluene, water and combinations thereof. In a specific example, temperatures can range from about 80° C. to about 120° C. In a specific example, reaction times can range from about 5 to 24 h. When the reaction occurs in acetic acid or acetic acid/water mixtures, typical temperatures for this reaction will be about 80 to about 110° C., for example from about 80 to 90° C., 90 to 100° C. or 100 to 110° C., and can occur from about 0.5 to about 4 hours, for example 0.5, 1, 1.5 2, or 4. This reaction can also be used to make compounds of formula I from compounds of formula III.

These methods can also involve (b) reacting a compound of formula V with a compound of formula VIa, optionally in a non-protic organic solvent and/or in the presence of a base, to make the compound of formula IIIa:

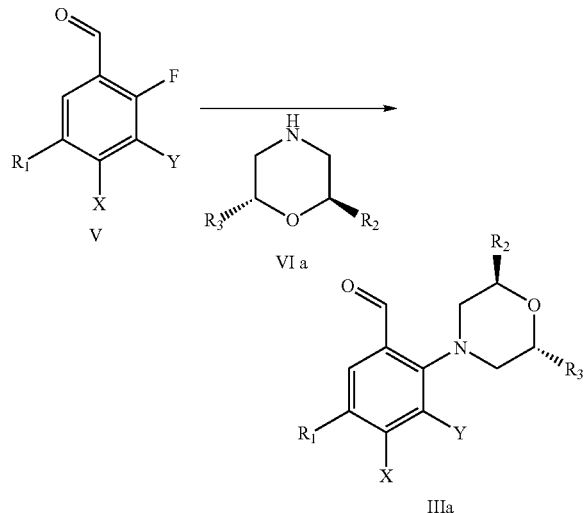

In this reaction, when present, the base can be an organic or inorganic base. In some instances compound VIa can act as a base. Typically, the reaction will take place at a temperature of about 20 to about 100° C., for example from about 40 to 100° C., 60 to 80° C. or 80 to 100° C. This reaction can also be performed alone to provide the compound of formula IIIa. Examples of solvents that can be used include acetonitrile and dimethylformamide. Temperature ranges for the reaction can also be about 70 to 90° C. Bases that can be used in the reaction include triethylamine, diisopropylethylamine and potassium carbonate. Reaction times can range from about 2 to 24 hours, for example 2, 4, 6, 8, 10, 12, 14, 16, 18, 20, 22 or 24 hours. This reaction can also be used to make a compound of formula III using a compound of formula VI.

Compound V can be made by:
(c)(i) performing a halogen metal exchange or deprotonation reaction on a compound of formula VII, and
(c)(ii) reacting the product of (c)(i) with a carbonyl donor to make the compound of formula V:

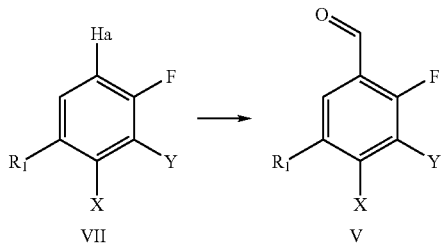

In the above, reaction, Ha is hydrogen or a halogen, for example bromine. Ha can also be chlorine or iodine. In this reaction, (c)(i) can include contacting the compound of formula VII with a strong base, such as an alkyl lithium. Alternatively, (c)(i) can include contacting the compounds of formula VII with a Grignard reagent in a non-protic organic solvent. These reactions typically occur at a temperature from about −78 to about 50° C., for example from about −78 to about 0° C. In (c)(ii) the carbonyl donor can include one or more of dimethylformamide, N-formylmorpholine, or para-nitrophenylformate. Examples of reaction times can be from about 1 to about 18 hours, for example 2, 4, 6, 8, 10, 12, 14, 16 or 18 hours.

Compound V can also be synthesized by (d) oxidizing a compound of formula VIII to make the compound of formula V:

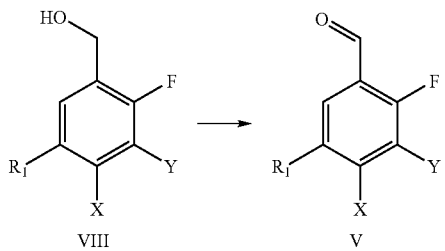

One synthesis can combine several of these steps as follows:

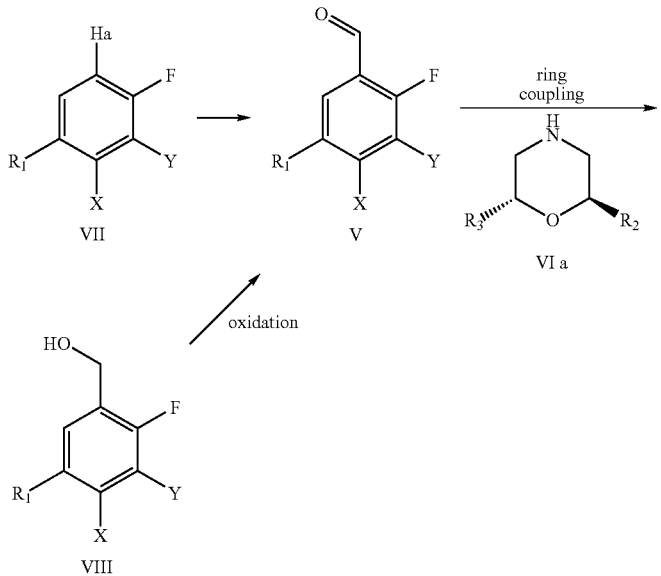

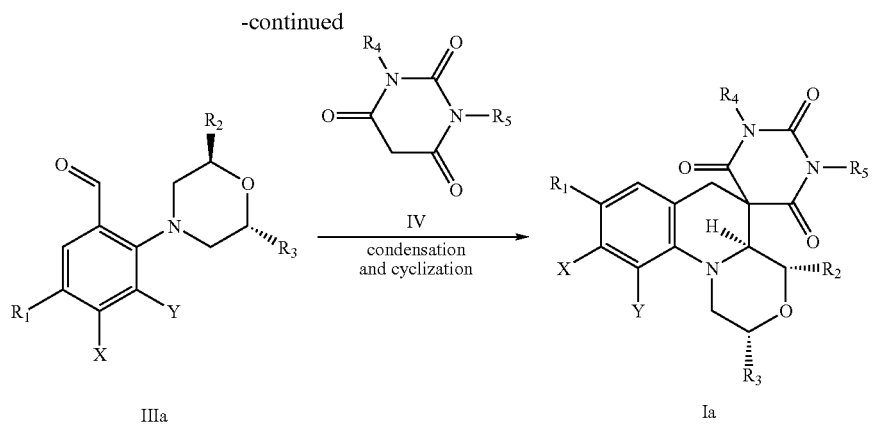

Described compounds and intermediates can also be produced according to the following reaction:

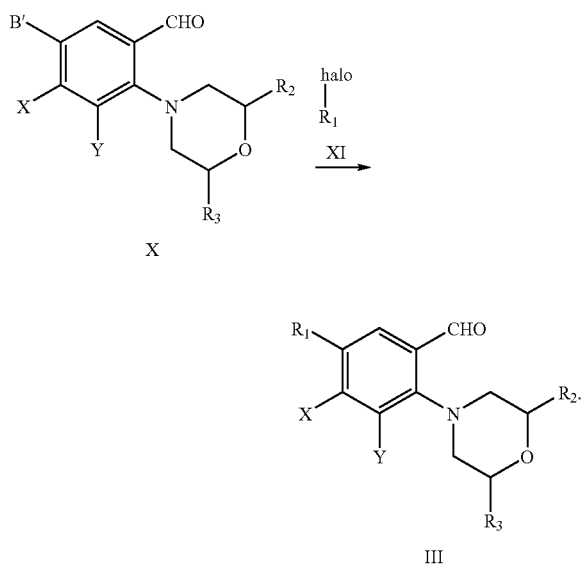

In this reaction, B' is boronic acid or a boronate ester, such as

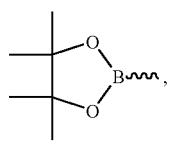

and halo is a halogen, such as iodine. Accordingly, compound III is made by reacting compounds X and XI. This coupling reaction can also be performed with reverse polarity wherein the boron is attached to $R_1$ and the halogen is attached to compound X at the position indicated by B' (see structure XII below). In general, the coupling reaction can be performed under standard Suzuki cross-coupling conditions employing 0.01-0.1 equivalents of a palladium catalyst with appropriate ligands, such as $Pd(PPh_3)_4$ or $Pd(dppf) Cl_2$, in an organic solvent or solvent mixture containing organic solvents, such as toluene and an alcohol, and water. The reaction can be performed in the presence of a base such as potassium carbonate, sodium carbonate, potassium phosphate, cesium carbonate or sodium acetate for example, at temperatures, e.g. from about 20 to 120° C. for about 2 to 24 h. This route can also be used to make compounds of formula IIIa when a trans-morpholine compound is used in the reaction. Compounds III or IIIa can be used to make compounds of formula I or Ia according to the methods described herein.

Compound X can be made by reacting compound XII to provide compound X, where halo is a halogen, such as bromine, chlorine or iodine:

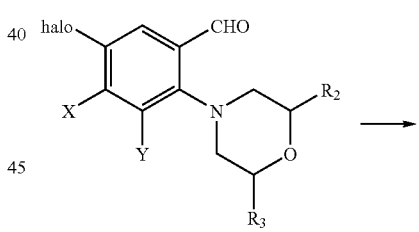

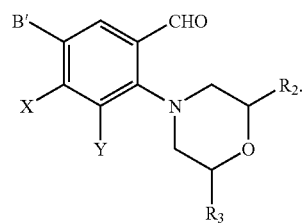

Conversion of compounds XII to compound X can be performed by reaction with a borane such as for example, bis(pinacolato)diboron, under palladium catalysis employing a palladium(II) or palladium(o) species with appropriate ligands, for example Pd(PPh$_3$)4, Pd(dppf)Cl$_2$, Pd(Pcy)$_2$Cl$_2$, in an organic solvent such as tetrahydrofuran, methyl-tetrahydrofuran, or toluene, and in the presence of an inorganic base such as, for example, potassium acetate, potassium phosphate, sodium carbonate, cesium carbonate. The reaction typically proceeds at elevated temperatures from 80 to 120° C. over about 12 h to 5 days.

In turn, compound XII can be made by reacting compounds VI and XIV, where halo is a halogen, such as bromine, chlorine or iodine:

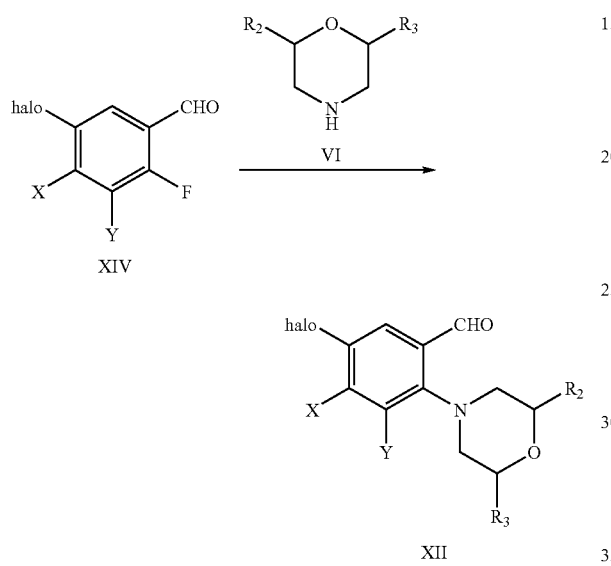

The method can involve (a) reacting a compound of formula XIV with a compound of formula VI, optionally in a non-protic organic solvent and/or in the presence of a base, to make the compound of formula XII. In this reaction, when present, the base can be an organic or inorganic base. In some instances compound VI can act as a base. Typically, the reaction will take place at a temperature of about 20 to about 100° C., for example from about 40 to 100° C., 60 to 80° C. or 80 to 100° C.

Compound XIV can be made from compound XV as follows, where halo is a halogen, such as bromine or iodine:

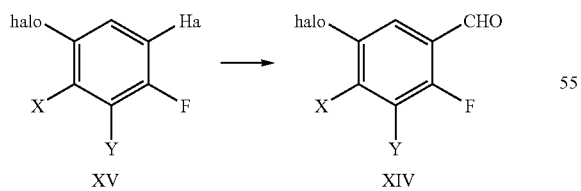

In one embodiment, compound XIV can be made by:
(b)(i) performing a deprotonation reaction on a compound of formula XV; and
(b)(ii) reacting the product of (b)(i) with a carbonyl donor to make the compound of formula XIV: In the above, reaction, Ha is hydrogen. In this reaction, (b)(i) can include contacting the compound of formula XV with a strong base, such as alkyl lithium. These reactions typically occur at a temperature from about −78 to about 50° C. In (b)(ii) the carbonyl donor can include one or more of dimethylformamide, N-formylmorpholine, or para-nitrophenylformate.

Also provided is a method of making the compound of formula XVIIa that includes
(a) reacting a compound of formula VIa with a compound of formula XVIII, optionally in a non-protic organic solvent and/or in the presence of a base, to make the compound of formula XVII.

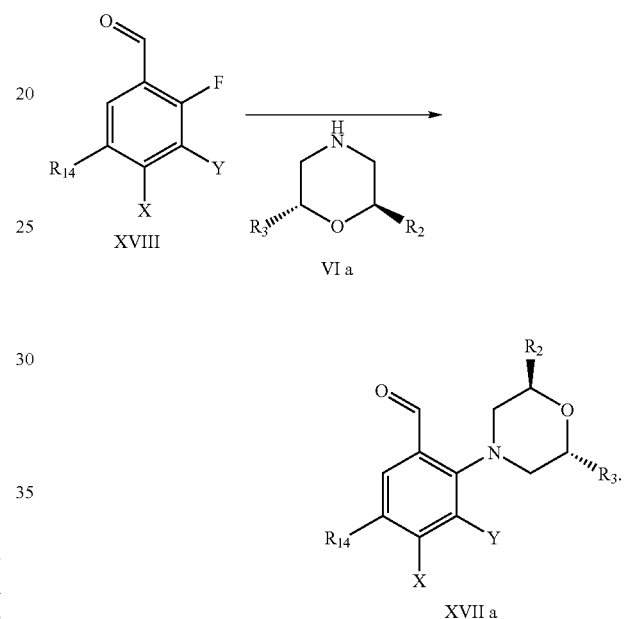

In this reaction, R$_{14}$ is a halogen, such as bromine or iodine, boronic acid, a boronate ester, such as

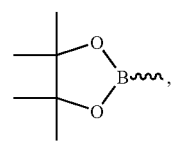

or a substituted or unsubstituted pyrazine, as in R$_1$.

In this reaction, when present, the base can be an organic or inorganic base. In some instances compound VIa can act as a base. Typically, the reaction will take place at a temperature of about 20 to about 100° C., for example from about 40 to 100° C., 60 to 80° C. or 80 to 100° C. Examples of solvents that can be used include acetonitrile and dimethylformamide. Temperatures ranges for the reaction can also be about 70 to 90° C. Bases that can be used in the reaction include triethylamine, diisopropylethylamine or potassium carbonate. Reaction times can range from about 2 to 24 hours, for example 2, 4, 6, 8, 10, 12, 14, 16, 18, 20, 22 or 24 hours.

When $R_{14}$ is a halogen, such as bromine, compound XVII can be used to make compound XVII where $R_{14}$ is boronic acid or a boronate ester using the same reaction as set forth for making compound X.

When $R_{14}$ is a halogen, such as iodine, compound XVII can also be used to make the compound of formula IIIa by coupling compound XVII with a compound of formula $R_1$—B', where B' is boronic acid or a boronate ester, such as

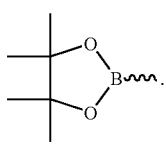

The compound of formula IIIa can also be produced when $R_{14}$ is boronic acid or a boronate ester, by reaction compound XVII with compound XI ($R_1$-halo) by the method set forth for making compound III described herein.

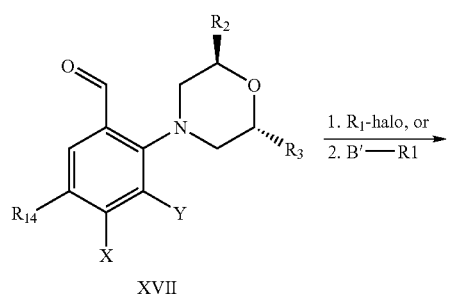

XVII

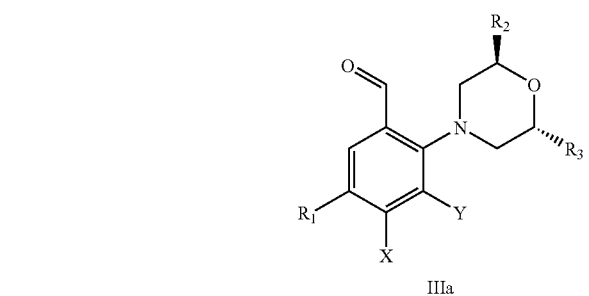

IIIa

In general, this coupling reaction can be performed under standard Suzuki cross-coupling conditions employing 0.01- 0.1 or more equivalents of a palladium catalyst with appropriate ligands, such as $Pd(PPh_3)_4$ or $Pd(dppf) Cl_2$, in an organic solvent or solvent mixture containing organic solvents, such as toluene and an alcohol, and water. The reaction can be performed in the presence of a base, such as potassium carbonate, sodium carbonate, potassium phosphate, cesium carbonate or sodium acetate for example, at temperatures, e.g. from about 20 to 120° C. for about 2 to 24 h. Compound III can then be used to produce compounds of Formula Ia as described herein.

Compound XVIII can be made by:
(b)(i) performing a halogen metal exchange or deprotonation reaction on a compound of formula XIX, and
(c)(ii) reacting the product of (c)(i) with a carbonyl donor to make the compound of formula XVIII:

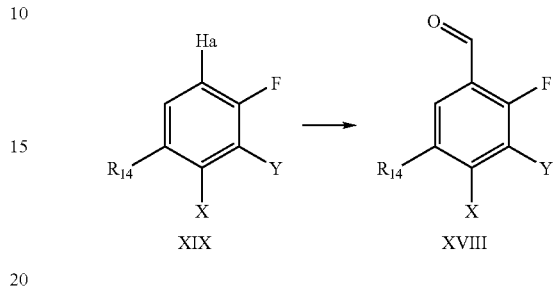

In the above, reaction, Ha is hydrogen or a halogen, for example bromine. Ha can also be chlorine or iodine. In this reaction, (c)(i) can include contacting the compound of formula XIX with a strong base, such as alkyl lithium. Alternatively, (c)(i) can include contacting the compounds of formula XIX with a Grignard reagent in a non-protic organic solvent. These reactions typically occur at a temperature from about −78 to about 50° C., for example from about −78 to about 0° C. In (c)(ii) the carbonyl donor can include one or more of dimethylformamide, N-formylmorpholine or para-nitrophenylformate. Examples of reaction times can be from about 1 to about 18 hours, for example 2, 4, 6, 8, 10, 12, 14, 16 or 18 hours.

Compound XVIII can also be synthesized by (d) oxidizing a compound of formula XX to make the compound of formula XVIII:

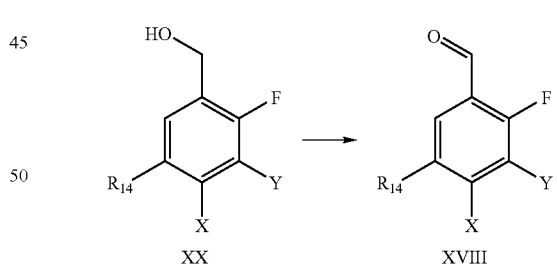

The compounds described herein can also be synthesized by appropriately modifying the protocols set forth in WO 2004/031195.

Certain compounds described herein are also useful as intermediates for preparing other described compounds and such intermediates are included within the scope of the present invention.

Specific compounds are described throughout with particular reference to the Examples and the following table, in which compounds starting with "rel-" or denoted by ±are racemic compounds:

TABLE 1

| Compound/Example No. | Name | Structure |
|---|---|---|
| 1 | rel-(2S,4R,4aR)-9,10-difluoro-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione | (±) |
| 2 | (2R,4S,4aS)-9,10-difluoro-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione | Chiral |
| 3 | (2S,4R,4aR)-9,10-difluoro-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione | Chiral |
| 4 | (2R,4S,4aS)-9,10-difluoro-2,4-dimethyl-1',3'-bis(morpholin-4-ylmethyl)-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione | Chiral |

TABLE 1-continued

| Compound/Example No. | Name | Structure |
|---|---|---|
| 5 | (2R,4S,4aS)-9,10-difluoro-2,4-dimethyl-1',3'-bis[(4-methylpiperazin-1-yl)methyl]-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione | 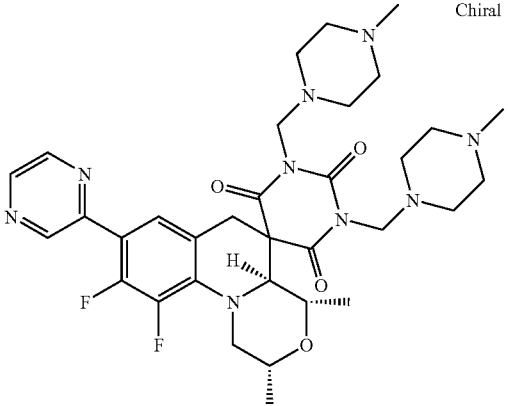 Chiral |
| 6 | (2R,4S,4aS)-9,10-difluoro-2,4-dimethyl-8-(4-oxidopyrazinpyrazin-2-yl)-1,2,4,4a-tetrahydro-2'H,6H-spiro[1,4-oxazino[4,3-a]quinoline-5,5'-pyrimidine]-2',4',6'(1'H,3'H)-trione | 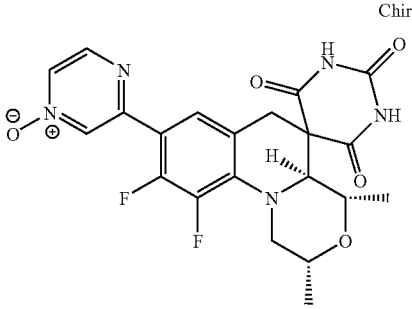 Chiral |
| 7 | rel-(2S,4R,4aR)-9,10-difluoro-2,4-dimethyl-2',4',6'-trioxo-8-pyrazin-2-yl-1,2,4,4a-tetrahydro-2'H,6H-spiro[1,4-oxazino[4,3-a]quinoline-5,5'-pyrimidine]-1',3'(4'H,6'H)-diyl]bis(methylene) diacetate | 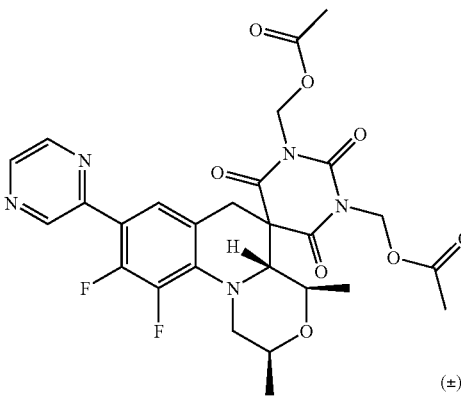 (±) |
| 8 | (2S,4R,4aR)-9,10-difluoro-2,4-dimethyl-2',4',6'-trioxo-8-pyrazin-2-yl-1,2,4,4a-tetrahydro-2'H,6H-spiro[1,4-oxazino[4,3-a]quinoline-5,5'-pyrimidine]-1',3'(4'H,6'H)-diyl]bis(methylene) diacetate | 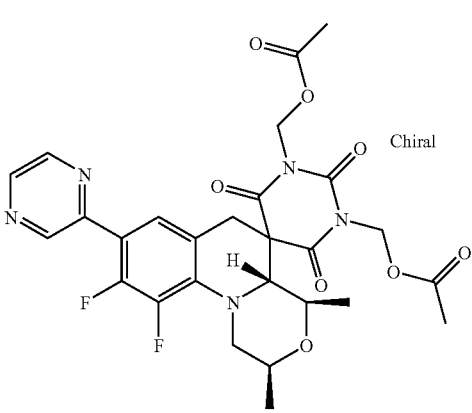 Chiral |

TABLE 1-continued

| Compound/<br>Example<br>No. | Name | Structure |
|---|---|---|
| 9 | rel-(2S,4R,4aR)-9,10-difluoro-1',3'-bis(hydroxymethyl)-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione | 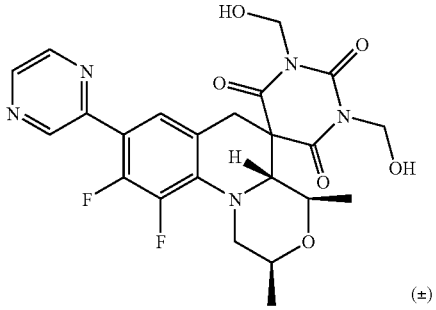 (±) |
| 10 | (2S,4R,4aR)-9,10-difluoro-1',3'-bis(hydroxymethyl)-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione | 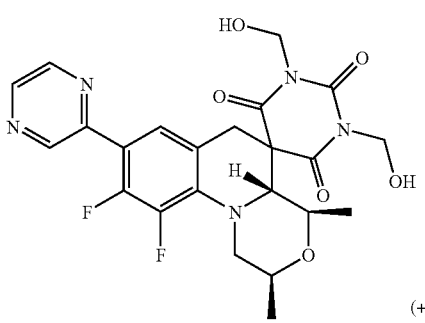 (+) |
| 11 | rel-(2S,4R,4aR)-1',3'-bix(chloromethyl)-9,10-difluoro-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione | 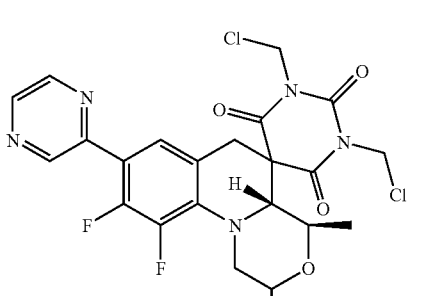 (±) |
| 12 | rel-tetrabenzyl [(2S,4R,4aR)-9,10-difluoro-2,4-dimethyl-2',4',6'-trioxo-8-pyrazin-2-yl-1,2,4,4a-tetrahydro-2'H,6H-spiro[1,4-oxazino[4,3-a]quinoline-5,5'-pyrimidine]-1',3'(4'H,6'H)-diyl]bis(methylene)bis(phosphate) | 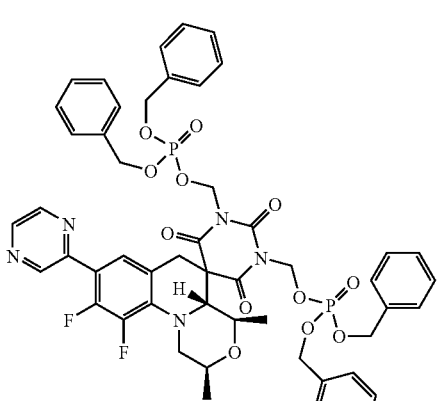 (±) |

TABLE 1-continued

| Compound/Example No. | Name | Structure |
|---|---|---|
| 13 | (2S,4R,4aR)-1',3'-bis(bromomethyl)-9,10-difluoro-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione | (+) |
| 14 | tetra-tert-butyl [(2S,4R,4aR)-9,10-difluoro-2,4-dimethyl-2',4',6'-trioxo-8-pyrazin-2-yl-1,2,4,4a-tetrahydro-2'H,6H-spiro[1,4-oxazino[4,3-a]quinoline-5,5'-pyrimidine]-1',3'(4'H,6'H)-diyl]bis(methylene)bis(phosphate) | (+) |
| 15 | rel-(2S,4R,4aR)-10-fluoro-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione | (±) |
| 16 | rel-(2S,4R,4aR)-10-fluoro-2,4-dimethyl-9-morpholin-4-yl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione | (±) |

TABLE 1-continued

| Compound/ Example No. | Name | Structure |
|---|---|---|
| 17 | rel-(2S,4R,4aR)-10-fluoro-9-(2-methoxyethoxy)-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione | (±) |
| 18 | rel-(2S,4R,4aR)-10-fluoro-9-(2-fluoroethoxy)-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione | (±) |
| 19 | rel-(2S,4R,4aR)-9-dluoro-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione | (±) |
| 20 | rel-(2S,4R,4aR)-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione | (±) |
| 21 | rel-(2S,4R,4aR)-8-(3-methoxypyrazin-2-yl)-2,4-dimethyl-1,2,4,4a-tetrahydro-2'H,6H-spiro[1,4-oxazino[4,3-a]quinoline-5,5'-pyrimidine]-2',4',6'(1'H,3'H)-trione | (±) |

TABLE 1-continued

| Compound/Example No. | Name | Structure |
|---|---|---|
| 22 | (2R,4S,4aS)-8-(5-aminopyrazin-2-yl)-9,10-difluoro-2,4-dimethyl-1,2,4,4a-tetrahydro-2'H,6H-spiro[1,4-oxazino[4,3-a]quinoline-5,5'-pyrimidine]-2',4',6'(1'H,3'H)-trione | 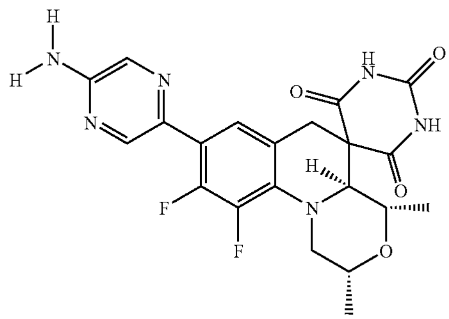 |
| 23 | (2R,4S,4aS)-9,10-difluoro-2,4-dimethyl-8-(5-methylpyrazin-2-yl)-1,2,4,4a-tetrahydro-2'H,6H-spiro[1,4-oxazino[4,3-a]quinoline-5,5'-pyrimidine]-2',4',6'(1'H,3'H)-trione | 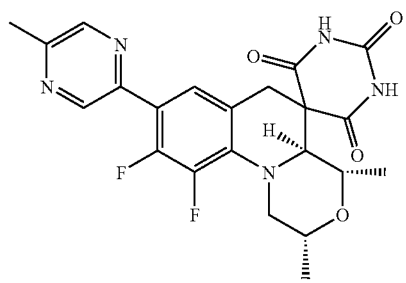 |
| 24 | (2R,4S,4aS)-8-(5-bromopyrazin-2-yl)-9,10-difluoro-2,4-dimethyl-1,2,4,4a-tetrahydro-2'H,6H-spiro[1,4-oxazino[4,3-a]quinoline-5,5'-pyrimidine]-2',4',6'(1'H,3'H)-trione | 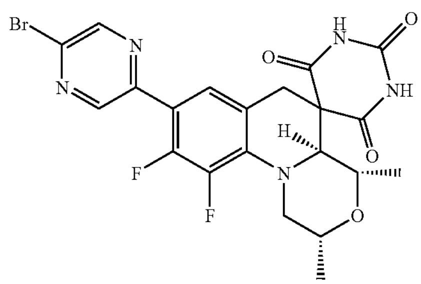 |
| 25 | (2R,4S,4aS)-9,10-difluoro-8-(5-methoxypyrazin-2-yl)-2,4-dimethyl-1,2,4,4a-tetrahydro-2'H,6H-spiro[1,4-oxazino[4,3-a]quinoline-5,5'-pyrimidine]-2',4',6'(1'H,3'H)-trione | chiral |
| 26 | (2R,4S,4aS)-8-(5-ethoxypyrazin-2-yl)-9,10-difluoro-2,4-dimethyl-1,2,4,4a-tetrahydro-2'H,6H-spiro[1,4-oxazino[4,3-a]quinoline-5,5'-pyrimidine]-2',4',6'(1'H,3'H)-trione | chiral |

Also provided are compositions that can be prepared by mixing one or more compounds described herein, or pharmaceutically acceptable salts or tautomers thereof, with pharmaceutically acceptable carriers, excipients, binders, diluents or the like, to treat or ameliorate a variety of bacterial infections. A therapeutically effective dose or amount refers to that amount of one or more compounds described herein sufficient to result in amelioration of symptoms of the infection. The pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsule syrup, suppositories, injections, emulsions, elixirs, suspensions or solutions. The instant compositions can be formulated for various routes of administration, for example, by oral administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments can be added for identification. Tablets and pills can be further treated with suitable coating materials known in the art.

Liquid dosage forms for oral administration can be in the form of pharmaceutically acceptable emulsions, syrups, elixirs, suspensions, slurries and solutions, which can contain an inactive diluent, such as water. Pharmaceutical formulations can be prepared as liquid suspensions or solutions using a sterile liquid, such as, but not limited to, an oil, water, an alcohol, and combinations of these. Pharmaceutically suitable surfactants, suspending agents, emulsifying agents, can be added for oral or parenteral administration.

As noted above, suspensions can include oils. Such oils include peanut oil, sesame oil, cottonseed oil, corn oil, olive oil and mixtures of oils. Suspension preparation can also contain esters of fatty acids such as ethyl oleate, isopropyl myristate, fatty acid glycerides and acetylated fatty acid glycerides. Suspension formulations can include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water can also be used in suspension formulations.

For nasal administration, the pharmaceutical formulations can be a spray or aerosol containing and appropriate solvents and optionally other compounds such as, but not limited to, stabilizers, antimicrobial agents, antioxidants, pH modifiers, surfactants, bioavailablity modifiers and combinations of these. A propellant for an aerosol formulation can include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms generally include aqueous suspensions or oil suspensions which can be prepared using a suitable dispersant or wetting agent and a suspending agent. Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Generally, the oil or fatty acid is nonvolatile, including natural or synthetic oils, fatty acids, mono-, di- or tri-glycerides.

For injection, the pharmaceutical formulation can be a powder suitable for reconstitution with an appropriate solution as described above. Examples of these include freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

For rectal administration, the pharmaceutical formulations can be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils can also be employed in the preparation of formulations of the soft gelatin type and suppositories. Water, saline, aqueous dextrose and related sugar solutions, and glycerols can be employed in the preparation of suspension formulations which can also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carries are generally known to those skilled in the art and are thus included in the instant invention. Such excipients and carriers are described, for example, in "Remingtons Pharmaceutical Sciences" Mack Pub. Co., New Jersey (1991).

The formulations of the invention can be designed for to be short-acting, fast-releasing, long-acting, and sustained-releasing. Thus, the pharmaceutical formulations can also be formulated for controlled release or for slow release.

The instant compositions can also comprise, for example, micelles or liposomes, or some other encapsulated form, or can be administered in an extended release form to provide a prolonged storage and/or delivery effect. Therefore, the pharmaceutical formulations can be compressed into pellets or cylinders and implanted intramuscularly or subcutaneously as depot injections or as implants such as stents. Such implants can employ known materials such as silicones and biodegradable polymers.

The compositions can contain, for example, from about 0.1% by weight, to about 90% or more by weight, of the active material, depending on the method of administration. Where the compositions comprise dosage units, each unit can contain, for example, from about 5 to 500 mg or more of the active ingredient. The dosage as employed for adult human treatment can range, for example, from about 10 to 3000 mg per day, depending on the route and frequency of administration.

Specific dosages can be adjusted depending on conditions of infection, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention. Generally, the total daily dose can typically range from about 0.1 mg/kg/day to about 500 mg/kg/day in single or in divided doses. Typically, dosages for humans can range from about 10 mg to about 3000 mg per day, in a single or multiple doses.

A therapeutically effective dose or amount can vary depending upon the route of administration and dosage form. Some compositions of the instant invention provide a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ can be determined by standard pharmaceutical procedures in animal cell cultures or experimental models.

In one embodiment, the invention provides methods of treating or preventing a bacterial infection in a subject, such as a mammal, e.g., a human or non-human mammal, comprising administering an effective amount of one or more compounds described herein to the subject. Suitable subjects that can be treated include domestic or wild animals, companion animals, such as dogs, cats and the like; livestock, including horses, cows and other ruminants, pigs, poultry, rabbits and the like; primates, for example monkeys, such as rhesus monkeys and cynomolgus (also known as crab-eating or long-tailed) monkeys, marmosets, tamarins, chimpanzees, macaques and the like; and rodents, such as rats, mice, gerbils, guinea pigs and the like. In one embodiment, the compound is administered in a pharmaceutically acceptable form, optionally in a pharmaceutically acceptable carrier. The compounds described herein can be used for the treatment or prevention of infectious disorders caused by a variety of bacterial organisms, including infections by pathogenic bacterial species. Examples include Gram positive and Gram negative aerobic and anaerobic bacteria, such as *Staphylococci*, e.g. *S. aureus*; *Enterococci*, e.g. *E. faecalis*; *Streptococci*, e.g. *S. pyogenes* and *S. pneumoniae*; *Escherichia* species, e.g. *E. coli*, including enterotoxigenic, enteropathogenic, enteroinvasive, enterohemorrhagic and enteroaggregative *E. coli* strains; *Haemophilus*, e.g. *H. influenza*; *Moraxella*, e.g. *M. catarrhalis*. Other examples include *Mycobacteria*, e.g. *M. tuberculosis, M. avian-intracellulare, M. kansasii, M. bovis, M. africanum, M. genavense, M. leprae, M. xenopi, M. simiae, M. scrofulaceum, M. malmoense, M. celatum, M. abscessus, M. chelonae, M. szulgai, M. gordonae, M. haemophilum, M. fortuni* and *M. marinum*; *Corynebacteria*, e.g. *C. diphtheriae*; *Vibrio* species, e.g. *V. cholerae*; *Campylobacter* species, e.g. *C. jejuni*; *Helicobacter* species, e.g. *H. pylori*; *Pseudomonas* species, e.g. *P. aeruginosa*; *Legionella* species, e.g. *L. pneumophila*; *Treponema* species, e.g. *T. pallidum*; *Borrelia* species, e.g. *B. burgdorferi*; *Listeria* species, e.g. *L. monocytogenes*; *Bacillus* species, e.g. *B. cereus*; *Bordatella* species, e.g. *B. pertussis*; *Clostridium* species, e.g. *C. perfringens, C. tetani, C. difficile* and *C. botulinum*; *Neisseria* species, e.g. *N. meningitidis* and *N. gonorrhoeae*; *Chlamydia* species, e.g. *C. psittaci, C. pneumoniae* and *C. trachomatis*; *Rickettsia* species, e.g. *R. rickettsii* and *R. prowazekii*; *Shigella* species, e.g. *S. sonnei*; *Salmonella* species, e.g. *S. typhimurium*; *Yersinia* species, e.g. *Y. enterocolitica* and *Y. pseudotuberculosis*; *Klebsiella* species, e.g. *K. pneumoniae*; and *Mycoplasma*, e.g. *M. pneumoniae*.

Infections that can be treated with the described compounds include central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients. These infections can be treated in hospital or community settings via various routes of administration as described herein.

The compounds or compositions described herein can also be used prophylactically. Accordingly, one or more of the present compounds or compositions can be administered to an individual deemed to be at risk for developing a microbial infection. Individuals at risk for developing a microbial infection include individuals who have been exposed to a particular microorganism, such as a pathogenic bacterial species; individuals having a compromised immune system, such as individuals suffering from an immunodeficiency disease or taking immunocompromising medication; and individuals having a history of repeated or chronic infection, such as children who have repeated infections of the middle ear.

Another embodiment provides a method of killing or preventing the growth of bacteria that includes contacting a bacteria with either a non-therapeutic amount or a therapeutically effective amount of one or more of the present compounds. Such methods can occur in vivo or in vitro. In vitro contact can involve a screening assay to determine the efficacy of the one or more compounds against selected bacteria at various amounts or concentrations. In vivo contact with a therapeutically effective amount of the one or more compounds can involve treatment or prophylaxis of a bacterial infection in the animal in which the contact occurs. The effect of the one or more compounds on the bacteria and/or host animal can also be determined or measured.

Included within the scope of the invention are all isomers (e.g. stereoisomers, diastereoisomers, epimers, geometrical isomers) of the compounds described herein as well as any wholly or partially equilibrated mixtures thereof (e.g. racemic or optically active mixtures). The present invention also covers the individual isomers of the compounds represented by the formulas herein as mixtures with isomers thereof in which one or more chiral centers are inverted.

Stereoisomeric mixtures, e.g. mixtures of diastereomers, can be separated into their corresponding isomers in a known manner by means of suitable separation methods. Diastereomeric mixtures for example can be separated into their individual diastereomers by means of fraction crystallization, chromatography, solvent distribution, and similar procedures. This separation can take place either at the level of one of the starting compounds or in a compound of formula I itself. Enantiomers can be separated through the formation of diastereomeric salts, for example by salt formation with an enantiomerically pure chiral acid, or by means of chromatography, for example by HPLC, using chiral chromatographic media.

It is understood that the compounds described herein can exhibit the phenomenon of tautomerism. As the chemical structures sometimes only represent one of the possible tautomeric forms, it should be understood that the invention encompasses any tautomeric form of the represented structure.

In addition, the compounds described herein can exist in unsolvated as well as solvated forms with pharmaceutically acceptable solvents such as water, ethanol, and the like. In general, the solvated forms are considered equivalent to the unsolvated forms for the purposes of the present invention.

EXAMPLES

Example 1

Step 1: 2-Bromo-3,4,5-trifluorobenzaldehyde. A 3-L 4-neck flask was dried by heating with a hot air gun to 94-95° C. After cooling to room temperature, 74.48 grams (1.47 mol) diisopropylamine was added to the flask and dissolved in 600 ml dry THF. The solution was cooled to −75° C. and n-butyllithium (2.5 M in hexane, 320 ml) was added dropwise over 70 minutes while maintaining the temperature between −75 to −60° C. The mixture was allowed to warm to −10.4° C. to 0.2° C. for 13 minutes. The reaction was cooled to −73.7° C. and 140 grams (0.665 mol) of 1-bromo-2,3,4-trifluorobenzene dissolved in 860 ml THF was added dropwise over 2 hours while maintaining the temperature between −73.7° C. to −66° C. The reaction was allowed to stir for 5 hours between −76.3° C. to −71.7° C. DMF (146 ml) was added over 40 minutes at −70.2 to −64.8° C. The reaction was allowed to warm to 13° C. overnight. The reaction was cooled to −25.6° C. before adding dropwise a solution of 259 ml concentrated hydrochloric acid in 538 ml distilled water. The addition was complete in 30 minutes with the temperature getting no higher than −9° C. The layers were separated and the aqueous portion extracted three times with ml ethyl acetate. The combined organic portions were washed successively with 500 ml saturated $NaHCO_3$ solution and 500 ml brine. After drying over sodium sulfate, the mixture was filtered and rotary evaporated to give 148.4 grams of a brown liquid. The liquid was vacuum distilled and the product collected at 47.9-51.3° C. (1.6 torr), giving 110.17 grams product with 91% purity (HPLC). This was taken up in heptane and chilled in the freezer to yield 80.23 grams of white to light yellow solid. The solid was combined with a subsequent crop and material from an earlier pilot reaction to give 106.21 grams which was vacuum dried to remove heptane, yielding 104.95 grams with 98.8% purity, mp 36.8-38° C. HPLC analysis done on a Chromolith Performance, RP-18e, 100-4.6 mm. Mobil Phase: A=Methanol, B=0.1 N TEAA (pH=7). Gradient from 50% to 90% methanol over 5 minutes. Detector at 254 nm. Retention time: 1.79 minutes.

Step 2: 3-Bromo-6-(2,6-cis-dimethylmorpholin-4-yl)-4,5-difluorobenzaldehyde. 2-Bromo-3,4,5-trifluorobenzaldehyde (133.15 grams, 0.56 mol) was dissolved in 1000 ml dry acetonitrile. Triethylamine (118.65 ml, 0.85 mol) was added, followed by cis-2,6-dimethylmorpholine (Lancaster, 71.64 grams, 0.62 mol), and 125 ml additional acetonitrile. The mixture was refluxed for 24 hours, then cooled to room temperature, and poured into 1500 ml saturated sodium bicarbonate solution. The phases were separated and the aqueous phase extracted twice with 500 ml ethyl acetate. The combined organic portions were washed twice with 500 ml brine and then dried over magnesium sulfate. After filtering and rotary evaporation, 199.7 grams of oil was recovered. The oil was diluted to ~300 ml with heptane to induce solidification and placed in the freezer overnight. The resulting yellow solid was filtered to yield 111.7 grams, 99.8% purity (HPLC) of title compound. Mp 88.1-92.0° C. HPLC analysis done on a Chromolith Performance column, RP-18e, 100-4.6 mm; Mobile phase: A=MeOH, B=0.1N TEAA (pH=7); Gradient: 60% A to 100% A over 5 minutes; wavelength: 254 nm; Retention time: 1.94 minutes.

Step 3: 2-(2,6-Dimethyl-morpholin-4-yl)-3,4-difluoro-5-(4,4,5,5-tetramethyl-[1,3,2]dioxaborolan-2-yl)-benzaldehyde. Potassium acetate (179.7 grams, 1.83 mol), $Pd(PCy_3)_2Cl_2$ (Aldrich, 32.0 grams, 0.043 mol), bis-(pinacolato)diboron (Aldrich, 149.7 grams, 0.59 mol), and 3-Bromo-6-(2,6-cis-dimethylmorpholin-4-yl)-4,5-difluorobenzaldehyde (147.0 grams, 0.538 mol) were placed in a 5L 4-neck flask. The solids were evacuated and flushed with argon six times. Methyltetrahydrofuran (3300 ml) was added. The mixture was mechanically stirred as it was evacuated until bubbling stopped. The reactants were flushed with argon, then evacuated and flushed with argon again. Argon was bubbled through the mixture for 2 hours and 16 minutes. The mixture was evacuated until bubbling ceased, flushed with argon, evacuated, and flushed with argon again. The mixture was heated to reflux for 4.7 days, when NMR indicated that all 3-bromo-6-(2,6-cis-dimethylmorpholin-4-yl)-4,5-difluorobenzaldehyde had been consumed. The mixture was cooled to room temperature, filtered, and rinsed with ethyl acetate. The filtrate was rotary evaporated to give a sticky solid which was taken up in ethyl acetate and filtered. This yielded 101.9 grams of solid. The solids were mixed with ~800 ml warm ethyl acetate and filtered to remove catalyst. Rotary evaporation yielded 94.4 grams of product with satisfactory NMR. The initial ethyl acetate filtrate was concentrated, heptane was added to induce solidification, and the resulting mixture placed in a freezer. This was filtered to yield 45.45 grams of additional product. This was taken up with ~400 ml warm ethyl acetate, filtered to remove a white impurity, and then rotary evaporated. The residue was treated with hot heptane to yield fine particles and then filtered to collect additional product. Total product collected was 121 grams, mp 142.9-143.8° C. Anal. calcd.: 59.86%; C, 6.87%; H, 3.67%; N. Found: 59.81%; C, 7.03%; H, 3.66%; N.

Step 4: 2-(2,6-Dimethyl-morpholin-4-yl)-3,4-difluoro-5-pyrazin-2-yl-benzaldehyde. 2-(2,6-Dimethyl-morpholin-4-yl)-3,4-difluoro-5-(4,4,5,5-tetramethyl-[1,3,2]dioxaborolan-2-yl)-benzaldehyde (16 grams, 41 mmol), 2-iodopyrazine (Aldrich, 6 grams, 29.1 mmol), sodium carbonate (9.3 grams, 87 mmol) and $Pd(PPh_3)_2Cl_2$ (Aldrich, 0.82 gram, 1.2 mmol) were suspended in a 1:1 mixture of $CH_3CN/H_2O$. The reaction mixture was then purged with nitrogen and heated at 85° C. overnight. Upon completion the reaction was partitioned between $H_2O$ and ethyl acetate and the aqueous layer was extracted twice with ethyl acetate. The combined extracts were dried over $MgSO_4$, filtered and concentrated. The crude product was purified by column chromatography eluting with 5-40% ethyl acetate in hexanes to obtain 6.6 grams of the desired product. 1H NMR (400 MHz, CHLOROFORM-d) δ ppm 1.19 (d, J=6.2 Hz, 6H), 3.09 (m, 4H), 3.84 (m, 1H), 8.28

(dd, J=8.1, 2.1 Hz, 1H), 8.53 (d, J=2.5 Hz, 1H), 8.66 (dd, J=2.4, 1.7 Hz, 1H), 9.01 (s, 1 H), 10.22 (s, 1H); MS(APCl+) m/z 334 (MH+).

Step 5: Compound 1. A stirring slurry of 2-(2,6-Dimethyl-morpholin-4-yl)-3,4-difluoro-5-pyrazin-2-yl-benzaldehyde (6.6 grams, 19.9 mmol) in MeOH was treated with barbituric acid (Aldrich, 2.7 grams, 20.9 mmol). The reaction was refluxed overnight and cooled to room temperature. A solid precipitate resulted which was filtered and dried under vacuum to afford 7.2 grams of a pale yellow solid. 1H NMR (400 MHz, DMSO-d6) δ ppm 0.85 (d, J=6.4 Hz, 3H), 1.08 (d, J=6.2 Hz, 3H), 2.87 (d, J=14.4 Hz, 1H), 3.02 (m, 1H), 3.52 (d, J=14.8 Hz, 1H), 3.60 (dd, J=8.7, 6.3 Hz, 1H), 3.72 (m, 1H), 3.82 (d, J=8.8 Hz, 1H), 4.04 (dd, J=13.5, 2.1 Hz, 1H), 7.39 (d, J=8.4 Hz, 1H), 8.49 (d, J=2.5 Hz, 1H), 8.63 (dd, J=2.4, 1.7 Hz, 1H), 8.88 (m, 1H), 11.44 (s, 1H), 11.78 (s, 1H); MS(APCl+) m/z 444 (MH+). Anal. calcd for $C_{21}H_{19}F_2N_5O_4 \cdot 0.27 H_2O$: C, 56.27; H, 4.39; N, 15.62. Found: C, 55.88; H, 4.28; N, 15.39.

Example 2A

Compound 2: The enantiomers of compound 1 were separated by reverse phase HPLC. The more retained enantiomer 2: [alphaD]=−239°. Anal. calcd for $C_{21}H_{19}F_2N_5O_4 \cdot 0.22 H_2O$: C, 56.38; H, 4.38; N, 15.65. Found: C, 56.66; H, 4.21; N, 15.26.

Example 2B

Step 1: $K_2CO_3$ was added to a vigorously stirred mixture of 2R,6R-(trans)-dimethyl-morpholine (from BASF) in acetone (100 ml). Benzyl bromide was added dropwise to the mixture resulting in an exothermic reaction. The reaction was allowed to cool and stirred 18 h at rt. A majority of the acetone was removed under vacuum and portioned with water (100 ml) and EtOAc (100 ml). The aqueous layer was extracted with EtOAc (100 ml), dried over $Na_2SO_4$ and concentrated. The product was distilled under reduced pressure at 120° C. (75-80 at 0.5 torr) providing a colorless oil of 4-Benzyl-2R,6R-(trans)-dimethyl-morpholine.

Step 2: 2,6-Dimethyl-morpholine, HCl Salt. 4-Benzyl-2R,6R-(trans)-dimethyl-morpholine (15 g, 73 mmol) was charged to an autoclave and MeOH (800 mL) added. Pd/C (3.5 g) was added and the mixture was stirred at room temperature overnight under 3.5 bars of pressure of $H_2$. The mixture was then filtered through celite followed by the addition of HCl 2M in $Et_2O$ (47 mL, 1.3 eq, 95 mmol). This filtrate was then concentrated to give the 8.3 g of the morpholine salt. 1H-NMR (500 MHz, CDCl$_3$) d 4.26 (m, 2H), 3.25 (m, 2H), 2.94 (m, 2H), 1.39 (m, 6H).

Step 3: 5-Bromo-2-(2,6-dimethyl-morpholin-4-yl)-3,4-difluoro-benzaldehyde. To a solution of 5-bromo-2,3,4-trifluoro-benzaldehyde (11.5 g, 48 mmol) in dry acetonitrile (180 mL) was added $Et_3N$ (16.7 mL, 120 mmol) and 2,6-dimethylmorpholine, HCl Salt (8.3 g, 53 mmol). The reaction mixture was refluxed for 24 h. The solution was allowed to cool to room temperature and then poured into a saturated solution of $NaHCO_3$. The phases were separated and the aqueous phase was extracted with EtOAc. The combined organic layers were washed with brine, dried over $MgSO_4$ and concentrated to give an orange oil (15 g). Slurry of the crude in heptane yielded 11.92 g of a yellow solid. 1H-NMR (500 MHz, CDCl$_3$) d 10.36 (s, 1H), 7.82 (dd, 1H), 4.19 (m, 2H), 3.3 (d, 2H), 2.97 (dd, 2H), 1.30 (d, 6H).

Step 4: 2-(2,6-Dimethyl-morpholin-4-yl)-3,4-difluoro-5-(4,4,5,5-tetramethyl-[1,3,2]dioxaborolan-2-yl)-benzaldehyde. 5-Bromo-2-(2,6-dimethyl-morpholin-4-yl)-3,4-difluoro-benzaldehyde (18.7 g, 55.6 mmol), bis-(pinacolato)-diboron (19.0 g, 74.4 mmol), potassium acetate (22.8 g, 231 mmol) and bis-(tricyclohexylphosphine)-dichloropalladium (4.0 g, 5.41 mmol) were placed in a 1 L-3-necked flask. The solids were flushed with argon and degassed anhydrous 2-methyl-THF (470 mL) was added with a cannula. The reaction mixture was refluxed for 5 days, cooled to room temperature, filtered through celite and evaporated to give a sticky solid which was taken up in EtOAc and filtered. The mother liquor was evaporated and the residue triturated in heptane. Filtration via a sinter funnel gave 5.05 g. The mother liquor was evaporated again; the residue was triturated in heptane and cooled to +4° C. Filtration via a sinter funnel gave 5.69 g. The mother liquor was evaporated again, the residue was triturated in a little heptane and cooled to −18° C. Filtration using a sinter funnel gave 0.779 g. 1H-NMR (500 MHz, CDCl$_3$) d 10.25 (s, 1H), 7.98 (dd, 1H), 4.20 (m, 2H), 3.38 (dt, 2H), 3.00 (m, 2H), 1.35 (s, 12H), 1.29 (d, 6H).

Step 5: 2-(2,6-Dimethyl-morpholin-4-yl)-3,4-difluoro-5-pyrazin-2-yl-benzaldehyde. To a suspension of 2-(2,6-Dimethyl-morpholin-4-yl)-3,4-difluoro-5-(4,4,5,5-tetramethyl-[1,3,2]dioxaborolan-2-yl)-benzaldehyde (11.5 g, 29.1 mmol) and sodium carbonate (8.8 g, 83.1 mmol) in previously degassed acetonitrile/water (1/1) mixture (140 mL) was added iodopyrazine (5.7 g, 27.7 mmol) under nitrogen. Bis-(triphenylphosphine)-dichloro-palladium-(II) (758 mg, 1.08 mmol) was added at room temperature and the reaction was heated overnight at 85° C. The mixture was cooled to room temperature, diluted with EtOAc and water. The phases were separated and the aqueous phase was re-extracted with EtOAc (×2). The combined organic layers were dried over $MgSO_4$ and concentrated to give a brown oil. Purification on silica gel (hexane/EtOAc 9/1, 8/2 then 7/3) yielded 3.65 g of an off-white solid. 1H-NMR (500 MHz, CDCl$_3$) d 10.35 (s, 1H), 9.06 (t, 1H), 8.70 (dd, 1H), 8.57 (d, 1H) 8.32 (dd, 1H), 4.24 (m, 2H), 3.43 (dt, 2H), 3.05 (m, 2H), 1.32 (d, 6H).

Step 6: Compound 2: (2R,4S,4aS)-9,10-difluoro-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione (2.65 g, 8 mmol) and barbituric acid (1.07 g, 8.4 mmol) were heated in IPA (350 mL) at 85° C. over 9½ days. A sample of the heterogeneous mixture was taken and evaporated to dryness. IPA (100 mL) was added and the reaction mixture was heated at 85° C. for further 2 days. A sample of the heterogeneous mixture was taken and evaporated to dryness. Further IPA (600 mL) was added to obtain a clear yellow solution and the reaction mixture was heated at 85° C. for an additional day. The solvent was then removed under reduced pressure affording 4 g of a yellow solid. The resulting solid was slurried in MeOH (100 mL) overnight and filtered to give 1.79 g of a yellow solid as a mixture of isomers. The mother liquor was evaporated to dryness and the resulting solid (2.17 g) was dissolved in MeCN (50 mL). Precipitation was achieved by adding water and filtration afforded pure product as a yellow solid (914 mg). 1H-NMR (500 MHz, DMSO-D6) d 11.83 (s, 1H), 11.49 (s, 1H), 8.94 (t, 1H), 8.68 (dd, 1H), 8.54 (d, 1H), 7.44 (d, 1H), 4.09 (dd, 1H), 3.88 (d, 1H), 3.77 (m, 1H), 3.66 (m, 1H), 3.57 (d, 1H), 3.07 (t, 1H), 2.92 (d, 1H), 1.13 (d, 3H), 0.91 (d, 3H); MS (APCl+, m/z) 443.1; Microanalysis: expected C, 55.88%; H, 4.32%; N, 15.79%. found C, 56.21%; H, 4.17%; N, 15.24%. The mixture of isomers (1.79 g) was suspended in IPA (700 mL) and heated at 85° C. for 5½ days. The solvent was then removed under reduced pressure affording an orange solid as a more enriched mixture of isomers. A combination of similar work-up as before (MeOH then MeCN/water) afforded two more batches of product (358 mg) and (150 mg) respectively.

Example 3

Compound 3: The enantiomers of compound 1 were separated by reverse phase HPLC. The less retained enantiomer 3: [alphaD]=+202°. Anal. calcd for $C_{21}H_{19}F_2N_5O_4 \cdot 0.05\, H_2O$: C, 56.77; H, 4.33; N, 15.76. Found: C, 56.38; H, 4.17; N, 15.43.

Example 4

Compound 4: Compound 2 (0.300 gram, 0.677 mmol) was suspended in dry acetonitrile (5 mL) and treated with formaldehyde (37% aqueous solution, 0.151 mL, 2.03 mmol) and morpholine (0.177 mL, 2.03 mmol). The suspension was heated at reflux overnight. The resulting solution was cooled and filtered to give a white solid. NMR indicated that starting material remained so the solid material was resuspended in acetonitrile and an additional amount of formaldehyde and morpholine was added. The reaction mixture was heated to reflux overnight. The solution was then cooled and the precipitate was filtered and dried to give a white solid (0.101 gram). 1H NMR (400 MHz, CHLOROFORM-d) δ ppm 0.98 (d, J=6.2 Hz, 3H), 1.19 (d, J=6.2 Hz, 3H), 2.48 (m, 4H), 2.69 (m, 4H), 3.00 (d, J=14.3 Hz, 1H), 3.08 (m, 1H), 3.18 (d, J=14.3 Hz, 1H), 3.51 (m, 4 H), 3.62 (m, 4H), 3.77 (m, 1H), 3.90 (m, 1H), 4.09 (d, J=8.6 Hz, 1H), 4.18 (dd, J=13.5, 2.0 Hz, 1H), 4.67 (d, J=13.1 Hz, 1H), 4.86 (dd, J=16.3, 13.0 Hz, 2H), 5.01 (d, J=13.1 Hz, 1H), 7.40 (d, J=6.8 Hz, 1H), 8.38 (d, J=2.3 Hz, 1H), 8.51 (m, 1H), 9.00 (s, 1H).

Example 5

Compound 5: Compound 2 (0.400 gram, 0.902 mmol) was suspended in dry acetonitrile (5 mL) and treated with formaldehyde (37% aqueous solution, 0.403 mL, 5.41 mmol)) and N-methylpiperazine (0.600 mL, 5.41 mmol). The suspension was heated under reflux for 5 hours. The resulting solution was cooled and concentrated to an oil. The oily residue was triturated several times with MTBE (tert-butyl methyl ether) and hexane to afford a precipitate that was filtered and dried under vacuum to obtain a yellow solid (0.438 gram). 1H NMR (400 MHz, CHLOROFORM-d) δ ppm 0.96 (d, J=6.4 Hz, 3 H), 1.18 (d, J=6.2 Hz, 3H), 2.12 (s, 3H), 2.22 (s, 3H), 2.46 (m, 8H), 2.69 (m, 4H), 3.12 (m, 3H), 3.77 (m, 1H), 3.89 (m, 1H), 4.08 (d, J=8.8 Hz, 1H), 4.17 (dd, J=13.5, 2.0 Hz, 1 H), 4.69 (d, J=12.9 Hz, 1H), 4.87 (dd, J=14.1, 13.3 Hz, 2H), 5.02 (d, J=12.9 Hz, 1H), 7.41 (d, J=7.6 Hz, 1H), 8.37 (d, J=2.5 Hz, 1H), 8.51 (m, 1H), 8.99 (s, 1H). Anal. calcd for $C_{33}H_{43}F_2N_9O_4 \cdot 0.55H_2O \cdot 0.20(CH_3)_3COCH_3$: C, 58.59; H, 6.76; N, 18.19. Found: C, 58.33; H, 7.23; N, 18.59.

Example 6

Compound 6: Compound 2 (0.400 gram, 0.90 mmol) was suspended in $CH_2Cl_2$ (40 mL) followed by the addition of 3-chloroperoxybenzoic acid (77% in $H_2O$). Reaction was stirred at room temperature for 2 days. Saturated sodium bicarbonate was then added. After stirring for 1 hour a yellow solid precipitate resulted which was filtered to obtain 0.188 gram of desired product. 1H NMR (400 MHz, DMSO-d6) δ ppm 0.84 (d, J=6.4 Hz, 3H), 1.07 (d, J=6.2 Hz, 3H), 2.83 (d, J=14.8 Hz, 1H), 3.00 (m, 1H), 3.36 (d, J=14.4 Hz, 1H), 3.62 (dd, J=8.8, 6.4 Hz, 1H), 3.70 (m, 1H), 3.84 (d, J=8.8 Hz, 1H), 4.03 (dd, J=13.7, 2.1 Hz, 1H), 7.40 (d, J=7.8 Hz, 1H), 8.19 (dd, J=4.1, 1.6 Hz, 1H), 8.43 (s, 1 H), 8.49 (dd, J=4.1, 0.8 Hz, 1H), 11.38 (s, 2H); MS(APCl+) m/z 460 (MH+). Anal. calcd for $C_{21}H_{19}F_2N_5O_5 \cdot 1.80H_2O \cdot 0.30CH_2Cl_2$: C, 49.45; H, 4.52; N, 13.54. Found: C, 49.26; H, 4.17; N, 13.15.

Example 7

Compound 7. Compound 1 (1.0 gram, 2.3 mmol) was dissolved in dry DMF (5 mL) and triethylamine (0.943 mL, 6.77 mmol) was added followed by bromomethyl acetate (Aldrich, 0.487 mL, 4.96 mmol). The resulting solution was stirred at room temperature overnight then diluted with ethyl acetate and washed with water. The organic layer was dried over $MgSO_4$, concentrated and purified by column chromatography eluting with 35-80% ethyl acetate in hexanes to give a yellow oil (0.942 gram) that was dried under vacuum. 1H NMR (400 MHz, DMSO-d6) δ ppm 0.85 (d, J=6.2 Hz, 3H), 1.09 (d, J=6.2 Hz, 3H), 1.84 (s, 3H), 2.00 (s, 3H), 3.00 (d, J=14.1 Hz, 1 H), 3.06 (dd, J=14.1, 9.2 Hz, 1H), 3.55 (d, J=14.3 Hz, 1H), 3.61 (dd, J=8.8, 6.4 Hz, 1H), 3.74 (m, 1H), 3.92 (d, J=8.6 Hz, 1H), 4.05 (dd, J=13.6, 2.2 Hz, 1H), 5.57 (q, J=10 Hz, 2H), 5.79 (q, J=10 Hz, 2H), 7.36 (d, J=7.8 Hz, 1H), 8.49 (d, J=2.5 Hz, 1H), 8.62 (dd, J=2.5, 1.6 Hz, 1H), 8.90 (m, 1H).

Example 8

Compound 8: To a cooled solution of compound 3 (2.0 gram, 4.5 mmol) in dry DMF (7 mL) was added triethylamine (1.89 mL, 13.5 mmol) followed by bromomethyl acetate (Aldrich, 1.42 mL, 14.4 mmol). The resulting solution was then heated to 50° C. for 3 hours. The reaction mixture was allowed to cool and then added drop wise to a stirring amount of water which afforded a precipitate that was filtered and dried under vacuum. 1H NMR (400 MHz, DMSO-d6) δ ppm 0.85 (d, J=6.2 Hz, 3H), 1.09 (d, J=6.2 Hz, 3H), 1.84 (s, 3H), 2.00 (s, 3H), 2.99 (d, J=14.8 Hz, 1H), 3.06 (m, 1H), 3.55 (d, J=14.3 Hz, 1H), 3.62 (m, 1H), 3.74 (m, 1H), 3.92 (d, J=8.6 Hz, 1H), 4.05 (dd, J=13.6, 2.2 Hz, 1H), 5.57 (m, 2H), 5.79 (m, 2H), 7.36 (d, J=7.8 Hz, 1H), 8.49 (d, J=2.5 Hz, 1H), 8.62 (dd, J=2.5, 1.6 Hz, 1H), 8.90 (m, 1H).

Example 9

Compound 9: A solution of compound 7 (0.940 gram, 1.60 mmol) in MeOH (20 mL) was treated with HCl (20 mL of a 1M solution in diethylether). The yellow solution was stirred for 1 hour resulting in a precipitate. The reaction mixture was concentrated. Ether was added and the resulting yellow solid was filtered and washed with ether. The solid material (0.755 gram) was dried under vacuum. 1H NMR (400 MHz, DMSO-d6) δ ppm 0.84 (d, J=6.2 Hz, 3H), 1.09 (d, J=6.1 Hz, 3H), 2.96 (d, J=14.6 Hz, 1H), 3.03 (m, 1 H), 3.40 (d, J=14.4 Hz, 1H), 3.62 (dd, J=8.7, 6.3 Hz, 1H), 3.73 (m, 1H), 3.89 (d, J=8.8 Hz, 1H), 4.06 (dd, J=13.5, 2.1 Hz, 1H), 4.95 (d, J=10.0 Hz, 1H), 5.04 (m, 1H), 5.21 (m, 2H), 5.86 (br. s., 2H), 7.32 (d, J=7.8 Hz, 1H), 8.49 (d, J=2.1 Hz, 1H), 8.63 (s, 1H), 8.89 (s, 1H).

Example 10

Compound 10: A solution of compound 8 (2.5 gram, 4.25 mmol) in MeOH (30 mL) was treated with HCl (30 mL of a 1 M solution in diethylether). The solution was stirred for 3 hours then concentrated and triturated several times with tert-butyl methyl ether to isolate a red solid. 1H NMR (400 MHz, DMSO-d6) δ ppm 0.84 (d, J=6.2 Hz, 3H), 1.09 (d, J=6.1 Hz, 3H), 2.96 (d, J=14.6 Hz, 1H), 3.01 (m, 1H), 3.40 (d, J=14.4 Hz, 1H), 3.62 (dd, J=8.7, 6.3 Hz, 1H), 3.73 (m, 1H), 3.89 (d, J=8.8 Hz, 1H), 4.06 (dd, J=13.5, 2.1 Hz, 1H), 4.95 (d, J=10.0 Hz, 1H), 5.04 (m, 1H), 5.21 (m, 2H), 5.86 (br. s., 2H), 7.32 (d, J=7.8 Hz, 1H), 8.49 (d, J=2.1 Hz, 1H), 8.63 (s, 1H), 8.89 (s, 1H).

Example 11

Compound 11: A solution of compound 9 (0.750 gram, 1.5 mmol) in $CH_2Cl_2$ was treated with thionyl chloride (1.1 mL). The reaction was stirred for 1 hour becoming a red solution. The solution was carefully quenched with water and stirred for 5 minutes. The organic layer was separated and the aqueous was extracted with $CH_2Cl_2$. The combined organics were dried over $MgSO_4$. Concentration provided the compound (0.657 gram) as a beige foam. 1H NMR (400 MHz, DMSO-d6) δ ppm 0.86 (d, J=6.3 Hz, 3H), 1.12 (d, J=5.5 Hz, 3H), 3.08 (m, 2H), 3.59 (m, 2H), 3.78 (m, 1H), 3.95 (d, J=8.6 Hz, 1H), 4.09 (dd, J=13.6, 2.2 Hz, 1H), 5.51 (m, 2H), 5.73 (s, 2H), 7.35 (d, J=8.0 Hz, 1H), 8.52 (d, J=2.3 Hz, 1H), 8.65 (dd, J=2.3, 1.6 Hz, 1H), 8.92 (m, 1H).

Example 12

Compound 12: To a mixture of dibenzyl phosphate (Aldrich, 0.770 gram, 2.8 mmol) and silver carbonate (0.383 gram, 1.4 mmol) in toluene (1 mL) was added compound 11 (0.600 gram, 1.1 mmol). The reaction mixture was heated to 70° C. for 2 hours then cooled to room temperature. The crude reaction mixture was loaded directly onto the column and purified by column chromatography eluting with 40-100% ethyl acetate in hexanes to obtain 0.439 g. 1H NMR (400 MHz, DMSO-d6) δ ppm 0.82 (d, J=6.4 Hz, 3H), 1.11 (d, J=6.1 Hz, 3H), 2.98 (d, J=14.7 Hz, 1H), 3.07 (m, 1H), 3.44 (d, J=14.1 Hz, 1H), 3.59 (dd, J=8.6, 6.4 Hz, 1H), 3.73 (m, 1H), 3.94 (d, J=8.8 Hz, 1H), 4.07 (dd, J=13.3, 1.8 Hz, 1H), 4.84 (m, 4H), 5.04 (dd, J=8.0, 2.0 Hz, 4H), 5.47 (m, 1H), 5.55 (t, J=9.9 Hz, 1H), 5.71 (t, J=9.8 Hz, 1H), 5.80 (m, 1H), 7.19 (m, 4H), 7.30 (m, 16H), 8.44 (d, J=2.5 Hz, 1H), 8.55 (m, 2H), 8.78 (s, 1H).

Example 13

Compound 13: To a stirring solution of compound 10 (0.10 gram, 0.20 mmol) and triphenylphosphine (0.16 gram, 0.60 mmol) in DMF (2 mL) was slowly added N-bromosuccinimide (NBS) (0.11 gram, 0.60 mmol) in dichloromethane (1 mL). The reaction mixture was stirred overnight at room temperature. The reaction was partitioned between water and dichloromethane. The combined organics were dried over $MgSO_4$. Purified by column chromatography eluting with ethyl acetate in hexanes (20-70%). Product was confirmed by the downfield shift of the methylene protons in the 1H NMR (400 MHz, DMSO-d6) δ ppm 5.47 (m, 2H), 5.69 (m, 2H).

Example 14

Compound 14: To a stirring solution of compound 10 (0.10 gram, 0.20 mmol) and triphenylphosphine (PL-TPP (Polymer Laboratories): 0.18 gram, 0.70 mmol) in THF (5 mL) was slowly added NBS (0.12 gram, 0.70 mmol). Reaction was stirred at room temperature for 1.5 hours then NaI (0.006 g, 0.04 mmol) was added followed by di-tertbutyl phosphate, potassium salt (Digital Specialty, 0.200 g, 0.79 mmol). Reaction was heated to 55° C. and a slurry resulted. An additional amount of THF (2 mL) was added and the reaction was heated for 3.5 hours. Filtered the reaction mixture and washed resin with $CH_2Cl_2$ and concentrated to a yellow oil. The oil was partitioned between $CH_2Cl_2$ and aqueous sodium bicarbonate then dried over $MgSO_4$. Triturated solid with hexane/MTBE and filtered light orange colored solid. 1H NMR (400 MHz, DMSO-d6) δ ppm 0.85 (d, J=6.2 Hz, 3H), 1.09 (d, J=6.1 Hz, 3H), 1.24 (d, J=4.9 Hz, 18H), 1.39 (s, 18H), 3.05 (m, 2H), 3.47 (d, J=14.8 Hz, 1H), 3.59 (dd, J=8.3, 6.2 Hz, 1H), 3.74 (m, 1H), 3.94 (d, J=8.4 Hz, 1H), 4.06 (dd, J=13.2, 1.5 Hz, 1H), 5.30 (m, 1H), 5.40 (m, 1H), 5.55 (m, 2H), 7.32 (d, J=7.0 Hz, 1H), 8.49 (d, J=2.5 Hz, 1H), 8.63 (m, 1H), 8.90 (s, 1H); MS(APCl+) m/z 888 (MH+).

Example 15

Step 1. 5-Bromo-2-(2,6-dimethyl-morpholin-4-yl)-3-fluoro-benzaldehyde. 4-(4-Bromo 2-[1,3]dioxolan-2-yl-6-fluoro-phenyl)-2,6-dimethyl-morpholine (1.0 grams, 2.8 mmol) was dissolved in THF (4 mL) and 1N HCl (3 mL). Stirred overnight at room temperature then heated to 50° C. for 5 hours. Reaction was partitioned between ethyl acetate and sodium bicarbonate. Dried the organic layer over $MgSO_4$, filtered and concentrated to obtain 0.847 gram of a yellow solid. 1H NMR (400 MHz, CHLOROFORM-d) δ ppm 1.19 (d, J=6.3 Hz, 6H), 2.90 (m, 2H), 3.01 (m, 2H), 3.81 (m, 2 H), 7.43 (dd, J=11.5, 2.2 Hz, 1H), 7.73 (dd, J=2.4, 1.2 Hz, 1H), 10.37 (s, 1H); MS(APCl+) m/z 316, 318 (MH+).

Step 2. 2-(2,6-Dimethyl-morpholin-4-yl)-3-fluoro-5-(4,4,5,5-tetramethyl-[1,3,2]dioxaborolan-2-yl)-benzaldehyde. 5-Bromo-2-(2,6-dimethyl-morpholin-4-yl)-3-fluoro-benzaldehyde (0.827 gram, 2.6 mmol) and bis(pinacolato)diboron (0.72 gram, 2.9 mmol) were dissolved in anhydrous 2-methyl-THF (20 mL). To this was added potassium acetate (0.770 gram, 7.8 mmol) and $Pd(PCy_3)_2Cl_2$ (0.058 gram, 0.08 mmol). The reaction mixture was ran under nitrogen and heated to 80° C. overnight. The reaction mixture was filtered and the filtrate was concentrated to a yellow solid. The crude product was purified by column chromatography eluting with ethyl acetate in hexanes to obtain 0.688 gram of the desired product. 1H NMR (400 MHz, CHLOROFORM-d) δ ppm 1.18 (d, J=6.3 Hz, 6H), 1.31 (s, 12H), 3.02 (m, 4H), 3.83 (m, 2H), 7.63 (dd, J=12.9, 1.5 Hz, 1 H), 8.01 (d, J=1.5 Hz, 1H), 10.32 (s, 1H); MS(APCl+) m/z 364 (MH+).

Step 3. 2-(2,6-Dimethyl-morpholin-4-yl)-3-fluoro-5-pyrazin-2-yl-benzaldehyde. 2-(2,6-Dimethyl-morpholin-4-yl)-3-fluoro-5-(4,4,5,5-tetramethyl-[1,3,2]dioxaborolan-2-yl)-benzaldehyde (0.40 gram, 1.1 mmol), 2-chloropyrazine (0.115 gram, 1.0 mmol), sodium carbonate (0.32 gram, 3.0 mmol) and $Pd(PPh_3)_2Cl_2$ (0.03 gram, 0.04 mmol) were suspended in a 1:1 mixture of $CH_3CN/H_2O$. The reaction mixture was then purged with Nitrogen and heated at 95° C. overnight. Upon completion the reaction was partitioned between $H_2O$ and ethyl acetate and the aqueous layer was extracted twice with ethyl acetate. The combined extracts were dried over $MgSO_4$, filtered and concentrated. The crude product was purified by column chromatography eluting with 10-55% ethyl acetate in hexanes to obtain 0.230 gram of the desired product. 1H NMR (400 MHz, CHLOROFORM-d) δ ppm 1.21 (d, J=6.3 Hz, 6H), 3.08 (m, 4H), 3.86 (m, 2H), 8.04 (dd, J=3.4, 2.2 Hz, 1H), 8.23 (d, J=1.5 Hz, 1H), 8.52 (d, J=2.4 Hz, 1H), 8.62 (dd, J=2.6, 1.6 Hz, 1H), 9.04 (d, J=1.5 Hz, 1H), 10.41 (s, 1H); MS(APCl+) m/z 316 (MH+).

Step 4. Compound 15: A stirring slurry of 2-(2,6-Dimethyl-morpholin-4-yl)-3-fluoro-5-pyrazin-2-yl-benzaldehyde (0.221 gram, 0.70 mmol) in MeOH (4 mL) was treated with barbituric acid (0.094 gram, 0.74 mmol). The reaction was refluxed overnight and cooled to room temperature. A solid precipitate resulted which was filtered and dried under vacuum to afford 0.246 gram of desired product. 1H NMR (400 MHz, DMSO-d6) δ ppm 0.87 (d, J=6.3 Hz, 3H), 1.09 (d, J=6.1 Hz, 3H), 2.98 (m, 2H), 3.48 (d, J=13.9 Hz, 1 H), 3.62 (dd, J=8.7, 6.5 Hz, 1H), 3.74 (m, 1H), 3.84 (d, J=8.8 Hz, 1H), 4.06 (dd, J=13.1, 1.8 Hz, 1H), 7.62 (d, J=1.2 Hz, 1H), 7.77 (dd, J=15.4, 2.0 Hz, 1H), 8.43 (d, J=2.4 Hz, 1 H), 8.55 (dd, J=2.6, 1.6 Hz, 1H), 9.08 (d, J=1.5 Hz, 1H), 11.45 (s, 1H), 11.81 (s, 1H); MS(APCl+) m/z 426 (MH+). Anal. calcd for $C_{21}H_{20}FN_5O_4 \cdot 0.52H_2O$: C, 58.01; H, 4.88; N, 16.11. Found: C, 57.62; H, 4.85; N, 15.88.

Example 16

Step 1a. 2-(2,6-Dimethyl-morpholin-4-yl)-3-fluoro-4-morpholin-4-yl-5-pyrazin-2-yl-benzaldehyde. To morpholine dissolved in $CH_3CN$ was added $K_2CO_3$ followed by 2-(2,6-Dimethyl-morpholin-4-yl)-3,4-difluoro-5-pyrazin-2-yl-benzaldehyde (Example 1, step 4). The reaction mixture was heated overnight. Partitioned between sodium bicarbonate and ethyl acetate. Extracted with ethyl acetate (3×), dried over $MgSO_4$ and concentrated. The crude product was purified by column chromatography eluting with 10-70% ethyl acetate in hexanes to obtain 0.099 gram of the desired product. 1H NMR (400 MHz, CHLOROFORM-d) δ ppm 1.21 (d, J=6.3 Hz, 6H), 3.06 (m, 8H), 3.60 (m, 4H), 3.85 (m, 2 H), 7.75 (d, J=1.6 Hz, 1H), 8.50 (d, J=2.5 Hz, 1H), 8.64 (m, 1H), 8.91 (s, 1H), 10.26 (s, 1H); MS(APCl+) m/z 401 (MH+).

Step 2. Compound 16: A stirring slurry of 2-(2,6-Dimethyl-morpholin-4-yl)-3-fluoro-4-morpholin-4-yl-5-pyrazin-2-yl-benzaldehyde (0.099 gram, 0.25 mmol) in MeOH was treated with barbituric acid (0.033 gram, 0.26 mmol). The reaction was refluxed overnight and cooled to room temperature. A solid precipitate resulted which was filtered and dried under vacuum to afford 0.105 gram of desired product. 1H NMR (400 MHz, DMSO-d6) δ ppm 0.87 (d, J=6.4 Hz, 3H), 1.10 (d, J=6.3 Hz, 3H), 2.92 (m, 6H), 3.46 (m, 5 H), 3.64 (dd, J=8.8, 6.4 Hz, 1H), 3.78 (m, 2H), 4.01 (dd, J=13.1, 2.1 Hz, 1H), 7.00 (s, 1H), 8.43 (d, J=2.5 Hz, 1H), 8.57 (dd, J=2.5, 1.6 Hz, 1H), 8.94 (d, J=1.6 Hz, 1H), 11.40 (s, 1H), 11.74 (s, 1H); MS(APCl+) m/z 511 (MH+). Anal. calcd for $C_{25}H_{27}FN_6O_5 \cdot 0.80H_2O$: C, 57.20; H, 5.49; N, 16.01. Found: C, 57.14; H, 5.32; N, 15.61.

Example 17

Step 1a. 2-(2,6-Dimethyl-morpholin-4-yl)-3-fluoro-4-(2-methoxy-ethoxy)-5-pyrazin-2-yl-benzaldehyde. NaH was suspended in THF (4 mL) and cooled to 0° C. To this suspension was slowly added 2-methoxy-ethanol and the reaction was stirred for 15 minutes at room temperature. 2-(2,6-Dimethyl-morpholin-4-yl)-3,4-difluoro-5-pyrazin-2-yl-benzaldehyde (Example 1, step 4) was dissolved up into THF and was slowly added to the reaction. The reaction was heated to 50° C. for 1 hour then stirred at room temperature overnight. The reaction mixture was partitioned between sodium bicarbonate and ethyl acetate. Extracted with ethyl acetate (3×), dried over $MgSO_4$, and concentrated. The crude product was purified by column chromatography eluting with 10-70% ethyl acetate in hexanes to obtain 0.099 gram of the desired product. 1H NMR (400 MHz, CHLOROFORM-d) δ ppm 1.20 (d, J=6.3 Hz, 6H), 3.08 (m, 4H), 3.27 (s, 3H), 3.60 (m, 2H), 3.86 (m, 2H), 4.31 (m, 2H), 8.14 (d, J=1.8 Hz, 1H), 8.50 (d, J=2.0 Hz, 1H), 8.66 (s, 1H), 9.19 (s, 1H), 10.28 (s, 1H); MS(APCl+) m/z 390 (MH+).

Step 2. Compound 17: A stirring slurry of 2-(2,6-Dimethyl-morpholin-4-yl)-3-fluoro-4-(2-methoxy-ethoxy)-5-pyrazin-2-yl-benzaldehyde (0.092 gram, 0.24 mmol) in MeOH was treated with barbituric acid (0.032 gram, 0.25 mmol). The reaction was refluxed overnight, cooled to room temperature and concentrated. Solid was triturated with MeOH, filtered and dried under vacuum to afford 0.044 gram of desired product. 1H NMR (400 MHz, DMSO-d6) δ ppm 0.87 (d, J=6.3 Hz, 3H), 1.10 (d, J=6.3 Hz, 3H), 2.88 (d, J=14.3 Hz, 1H), 2.98 (m, 1H), 3.10 (s, 3H), 3.47 (m, 3H), 3.63 (dd, J=8.6, 6.4 Hz, 1 H), 3.75 (m, 1H), 3.81 (d, J=8.6 Hz, 1H), 4.04 (m, 2H), 4.12 (m, 1H), 7.29 (s, 1H), 8.43 (d, J=2.5 Hz, 1H), 8.58 (m, 1H), 9.09 (d, J=1.6 Hz, 1H), 11.41 (s, 1H), 11.76 (s, 1H); MS(APCl+) m/z 500 (MH+). Anal. calcd for $C_{24}H_{26}FN_5O_6 \cdot 0.07H_2O$: C, 57.56; H, 5.26; N, 13.99. Found: C, 57.17; H, 5.02; N, 13.70.

Example 18

Step 1a. 2-(2,6-Dimethyl-morpholin-4-y)-3-fluoro-4-(2-fluoro-ethoxy)-5-pyrazin-2-yl-benzaldehyde. NaH was suspended in THF (4 mL) and cooled to 0° C. To this suspension was slowly added 2-fluoroethanol and the reaction was stirred for 15 minutes at room temperature. 2-(2,6-Dimethyl-morpholin-4-yl)-3,4-difluoro-5-pyrazin-2-yl-benzaldehyde (Example 1, step 4) was dissolved up into THF and was slowly added to the reaction. The reaction was heated to 50° C. for 1 hour then stirred at room temperature overnight. The reaction mixture was partitioned between sodium bicarbonate and ethyl acetate. Extracted with ethyl acetate (3×), which was dried over $MgSO_4$, and concentrated. The crude product was purified by column chromatography eluting with 10-50% ethyl acetate in hexanes to obtain 0.103 gram of the desired product.

1H NMR (400 MHz, CHLOROFORM-d) δ ppm 1.21 (d, J=6.3 Hz, 6H), 3.09 (m, 4H), 3.87 (m, 2H), 4.40 (m, 2H), 4.61 (m, 2H), 8.12 (d, J=2.0 Hz, 1H), 8.52 (m, 1H), 8.66 (m, 1 H), 9.10 (s, 1H), 10.28 (s, 1H); MS(APCl+) m/z 378 (MH+).

Step 2. Compound 18: A stirring slurry of 2-(2,6-Dimethyl-morpholin-4-yl)-3-fluoro-4-(2-fluoro-ethoxy)-5-pyrazin-2-yl-benzaldehyde (0.103 gram, 0.27 mmol) in MeOH was treated with barbituric acid (0.036 gram, 0.29 mmol). The reaction was refluxed overnight, cooled to room temperature and concentrated. Solid was triturated with MeOH, filtered and dried under vacuum to afford 0.081 gram of desired product. 1H NMR (400 MHz, DMSO-d6) δ ppm 0.87 (d, J=6.3 Hz, 3H), 1.10 (d, J=6.3 Hz, 3H), 2.88 (d, J=14.3 Hz, 1H), 2.98 (m, 1H), 3.10 (s, 3H), 3.47 (m, 3H), 3.63 (dd, J=8.6, 6.4 Hz, 1H), 3.75 (m, 1H), 3.81 (d, J=8.6 Hz, 1H), 4.04 (m, 2H), 4.12 (m, 1H), 7.29 (s, 1H), 8.43 (d, J=2.5 Hz, 1H), 8.58 (m, 1H), 9.09 (d, J=1.6 Hz, 1H), 11.41 (s, 1H), 11.76 (s, 1H); MS(APCl+) m/z 488 (MH+). Anal. calcd for $C_{23}H_{23}F_2N_5O_5 \cdot 0.71 H_2O$: C, 55.22; H, 4.92; N, 14.0. Found: C, 54.84; H, 4.66; N, 13.84.

Example 19

Step 1. 5-Bromo-2-(2,6-dimethyl-morpholin-4-yl)-4-fluoro-benzaldehyde. 4-(4-Bromo 2-[1,3]dioxolan-2-yl-5-fluoro-phenyl)-2,6-dimethyl-morpholine (3.5 grams, 9.7 mmol) was dissolved in THF and 1N HCl (3 mL). Reaction was stirred overnight at 50° C. The reaction was partitioned between ethyl acetate and sodium bicarbonate. The organic layer was dried over $MgSO_4$, filtered and concentrated to obtain 2.9 gram of a yellow solid. 1H NMR (400 MHz, CHLOROFORM-d) δ ppm 1.21 (d, J=6.3 Hz, 6H), 2.60 (dd, J=12.0, 10.3 Hz, 2H), 3.05 (m, 2H), 3.88 (m, 2H), 6.81 (d, J=10.4 Hz, 1H), 7.97 (d, J=8.0 Hz, 1H), 10.10 (s, 1H); MS(APCl+) m/z 316, 318 (MH+).

Step 2. 2-(2,6-Dimethyl-morpholin-4-yl)-4-fluoro-5-(4,4,5,5-tetramethyl-[1,3,2]dioxaborolan-2-yl)-benzaldehyde. 5-Bromo-2-(2,6-dimethyl-morpholin-4-yl)-4-fluoro-benzaldehyde (2.99 gram, 9.5 mmol) and bis(pinacolato)diboron (2.4 gram, 9.5 mmol) were dissolved in anhydrous 2-methyl-THF. To this was added potassium acetate (2.8 gram, 28 mmol) and Pd(PCy$_3$)$_2$Cl$_2$ (0.28 gram, 0.04 mmol). The reaction mixture was run under nitrogen and heated to 80° C. overnight. The reaction mixture was filtered and the filtrate was concentrated to a yellow solid. The crude product was purified by column chromatography eluting with ethyl acetate in hexanes to obtain 2.1 gram of product. 1H NMR (400 MHz, CHLOROFORM-d) δ ppm 1.21 (d, J=6.3 Hz, 6H), 1.33 (s, 12H), 2.61 (dd, J=12.1, 10.4 Hz, 2H), 3.18 (m, 2H), 3.90 (m, 2H), 6.62 (d, J=11.5 Hz, 1 H), 8.19 (d, J=7.2 Hz, 1H), 10.03 (s, 1H); MS(APCl+) m/z 364 (MH+).

Step 3. 2-(2,6-Dimethyl-morpholin-4-yl)-4-fluoro-5-pyrazin-2-yl-benzaldehyde. 2-(2,6-Dimethyl-morpholin-4-yl)-4-fluoro-5-(4,4,5,5-tetramethyl-[1,3,2]dioxaborolan-2-yl)-benzaldehyde (0.35 gram, 0.96 mmol), 2-iodopyrazine (79 μL, 0.80 mmol), potassium phosphate (0.34 gram, 1.6 mmol), Buchwald ligand: 2-(dicyclohexylphosphino)-2',6'-dimethoxy-1,1'-biphenyl (Strem Chemicals) (0.04 gram, 0.10 mmol), and Pd(OAc)$_2$ (Aldrich, 0.01 gram, 0.04 mmol) were suspended in Toluene (1.6 mL). The reaction mixture was then purged with Nitrogen and heated at 85° C. overnight. Upon completion the reaction was partitioned between H$_2$O and ethyl acetate and the aqueous layer was extracted twice with ethyl acetate. The combined extracts were dried over MgSO$_4$, filtered and concentrated. The crude product was purified by column chromatography eluting with 5-45% ethyl acetate in hexanes to obtain 0.230 gram of the desired product.

1H NMR (400 MHz, CHLOROFORM-d) δ ppm 1.24 (d, J=6.3 Hz, 6H), 2.68 (dd, J=11.9, 10.4 Hz, 2H), 3.21 (m, 2H), 3.94 (m, 2H), 6.82 (d, J=13.3 Hz, 1H), 8.53 (d, J=9.0 Hz, 2H), 8.67 (s, 1H), 9.05 (s, 1H), 10.14 (s, 1H); MS(APCl+) m/z 316 (MH+).

Step 4. Compound 19: A stirring slurry of 2-(2,6-Dimethyl-morpholin-4-yl)-4-fluoro-5-pyrazin-2-yl-benzaldehyde (0.115 gram, 0.36 mmol) in MeOH (4 mL) was treated with barbituric acid (0.049 gram, 0.38 mmol). The reaction was refluxed overnight, cooled to room temperature and concentrated. Solid was triturated with MeOH, filtered and dried under vacuum to afford 0.098 gram of desired product. 1H NMR (400 MHz, DMSO-d6) δ ppm 0.90 (d, J=6.4 Hz, 3H), 1.12 (d, J=6.1 Hz, 3H), 2.86 (m, 2H), 3.45 (d, J=14.8 Hz, 1 H), 3.50 (dd, J=8.9, 6.3 Hz, 1H), 3.57 (m, 1H), 3.76 (d, J=9.0 Hz, 1H), 4.12 (dd, J=12.8, 1.7 Hz, 1H), 6.87 (d, J=15.4 Hz, 1H), 7.55 (d, J=8.8 Hz, 1H), 8.43 (d, J=2.5 Hz, 1H), 8.61 (dd, J=2.5, 1.6 Hz, 1H), 8.88 (m, 1H), 11.45 (s, 1H), 11.75 (s, 1H); MS(APCl+) m/z 426 (MH+). Anal. calcd for C$_{21}$H$_{20}$FN$_5$O$_4$.1.23H$_2$O: C, 55.96; H, 4.99; N, 15.78. Found: C, 56.35; H, 5.06; N, 15.65.

Example 20

Step 1. 2-Fluoro-5-(4,4,5,5-tetramethyl-[1,3,2]dioxaborolan-2-yl)-benzaldehyde. 4-Fluoro-3-formylphenylboronic acid (Lancaster, 3.1 grams, 18 mmol) and pinacol (2.4 grams, 21 mmol) were stirred under nitrogen in anhydrous THF that contained activated 4 Å molecular sieves. Reaction was stirred overnight. The reaction mixture was filtered and the filtrate was concentrated in vacuo to give 4.5 grams of a white solid. 1H NMR (400 MHz, CHLOROFORM-d) δ ppm 1.32 (s, 12H), 7.14 (dd, J=10.5, 8.3 Hz, 1H), 8.00 (m, 1H), 8.31 (dd, J=7.4, 1.6 Hz, 1H), 10.34 (s, 1H); MS(APCl+) m/z 251 (MH+).

Step 2. 2-(2,6-Dimethyl-morpholin-4-yl)-5-(4,4,5,5-tetramethyl-[1,3,2]dioxaborolan-2-yl)-benzaldehyde. 2-Fluoro-5-(4,4,5,5-tetramethyl-[1,3,2]dioxaborolan-2-yl)-benzaldehyde (4.6 grams, 18 mmol) and potassium carbonate (3.8 grams, 27 mmol) were suspended in DMF (3 mL). Dimethyl morpholine (2.6 mL, 21 mmol) was then added and mixture was heated overnight at 105° C. Reaction mixture was cooled and filtered to remove salts. The dropwise addition of water induced formation of a precipitate. The yellow precipitate was filtered off and collected. Dried in vacuum oven to obtain 4.26 grams of desired product. 1H NMR (400 MHz, CHLOROFORM-d) δ ppm 1.21 (d, J=6.1 Hz, 6H), 1.32 (s, 12H), 2.65 (m, 2H), 3.16 (d, J=11.5 Hz, 2H), 3.93 (m, 2H), 7.03 (d, J=8.3 Hz, 1H), 7.90 (dd, J=8.2, 1.6 Hz, 1H), 8.22 (d, J=1.5 Hz, 1H), 10.17 (s, 1H); MS(APCl+) m/z 346 (MH+).

Step 3. 2-(2,6-dimethyl-morpholin-4-yl)-5-pyrazin-2-yl-benzaldehyde. 2-(2,6-dimethyl-morpholin-4-yl)-5-(4,4,5,5-tetramethyl-[1,3,2]dioxaborolan-2-yl)-benzaldehyde (0.250 grams, 0.72 mmol), 2-iodopyrazine (0.135 gram, 0.65 mmol), sodium carbonate (0.350 gram, 3.3 mmol) and Pd(PPh$_3$)$_2$Cl$_2$ (0.014 gram, 0.02 mmol) were suspended in a 1:1 mixture of CH$_3$CN/H$_2$O. The reaction mixture was then purged with Nitrogen and heated at 95° C. overnight. Upon completion the reaction was partitioned between H$_2$O and ethyl acetate and the aqueous layer was extracted twice with ethyl acetate. The combined extracts were dried over MgSO$_4$, filtered and concentrated. The crude product was purified by column chromatography eluting with 15-60% ethyl acetate in hexanes to obtain 0.157 gram of the desired product. 1H NMR (400 MHz, CHLOROFORM-d) δ ppm 1.25 (d, J=6.3 Hz, 6H), 2.73 (m, 2H), 3.20 (m, 2H), 3.95 (m, 2H), 7.20 (d, J=8.5 Hz, 1 H), 8.24 (dd, J=8.5, 2.4 Hz, 1H), 8.45 (d, J=2.4 Hz, 1H), 8.50 (d, J=2.4 Hz, 1H), 8.62 (m, 1H), 9.04 (d, J=1.5 Hz, 1H), 10.30 (s, 1H); MS(APCl+) m/z 298 (MH+).

Step 4. Compound 20: A stirring slurry of 2-(2,6-dimethyl-morpholin-4-yl)-5-pyrazin-2-yl-benzaldehyde (0.155 gram, 0.52 mmol) in IPA (4 mL) was treated with barbituric acid (0.070 gram, 0.55 mmol). The reaction was refluxed overnight and cooled to room temperature. A solid precipitate resulted which was filtered and dried under vacuum to afford 0.171 gram of desired product. 1H NMR (400 MHz, DMSO-d6) δ ppm 0.90 (d, J=6.3 Hz, 3H), 1.13 (d, J=6.1 Hz, 3H), 2.85 (dd, J=13.3, 10.4 Hz, 1H), 2.92 (d, J=15.1 Hz, 1H), 3.37 (d, J=14.9 Hz, 1H), 3.52 (dd, J=9.0, 6.3 Hz, 1H), 3.60 (m, 1H), 3.75 (d, J=9.0 Hz, 1H), 4.15 (dd, J=13.1, 2.1 Hz, 1H), 6.96 (d, J=9.0 Hz, 1H), 7.70 (d, J=2.0 Hz, 1H), 7.87 (dd, J=8.8, 2.2 Hz, 1H), 8.37 (d, J=2.7 Hz, 1H), 8.52 (dd, J=2.4, 1.5 Hz, 1H), 9.04 (d, J=1.5 Hz, 1H), 11.45 (s, 1H), 11.77 (s, 1H); MS(APCl+) m/z 408 (MH+). Anal. calcd for C$_{21}$H$_{21}$N$_5$O$_4$: C, 61.91; H, 5.20; N, 17.19. Found: C, 61.81; H, 5.13; N, 17.10.

Example 21

Step 1. 2-(2,6-Dimethyl-morpholin-4-yl)-5-(3-methoxy-pyrazin-2-yl)-benzaldehyde. 2-(2,6-dimethyl-morpholin-4-yl)-5-(4,4,5,5-tetramethyl-[1,3,2]dioxaborolan-2-yl)-benzaldehyde (Example 18, step 2) (0.250 gram, 0.72 mmol), 2-chloro-3-methoxypyrazine (0.095 gram, 0.66 mmol), sodium carbonate (0.350 gram, 3.3 mmol) and Pd(PPh$_3$)$_2$Cl$_2$ (0.014 gram, 0.02 mmol) were suspended in a 1:1 mixture of CH$_3$CN/H$_2$O. The reaction mixture was then purged with Nitrogen and heated at 95° C. overnight. Upon completion the reaction was partitioned between H$_2$O and ethyl acetate and the aqueous layer was extracted twice with ethyl acetate. The combined extracts were dried over MgSO$_4$, filtered and concentrated. The crude product was purified by column chromatography eluting with 15-45% ethyl acetate in hexanes to obtain 0.127 gram of the desired product. 1H NMR (400 MHz, CHLOROFORM-d) δ ppm 1.24 (d, J=6.3 Hz, 6H), 2.70 (m, 2H), 3.16 (m, 2H), 3.94 (m, 2H), 4.06 (s, 3H), 7.15 (d, J=8.5 Hz, 1H), 8.05 (d, J=2.7 Hz, 1H), 8.22 (d, J=2.7 Hz, 1H), 8.27 (dd, J=8.5, 2.2 Hz, 1H), 8.57 (d, J=2.2 Hz, 1H), 10.28 (s, 1H); MS(APCl+) m/z 328 (MH+).

Step 2. Compound 21: A stirring slurry of 2-(2,6-Dimethyl-morpholin-4-yl)-5-(3-methoxy-pyrazin-2-yl)-benzaldehyde (0.125 gram, 0.38 mmol) in nBuOH (4 mL) was treated with barbituric acid (0.051 gram, 0.40 mmol). The reaction was refluxed overnight, cooled to room temperature and concentrated. Triturated with MeOH and the precipitate was filtered and dried under vacuum to afford 0.071 gram of desired product.

1H NMR (400 MHz, DMSO-d6) δ ppm 0.90 (d, J=6.3 Hz, 3H), 1.13 (d, J=6.1 Hz, 3H), 2.84 (m, 1H), 2.91 (d, J=15.1 Hz, 1H), 3.38 (d, J=14.9 Hz, 1H), 3.52 (dd, J=8.4, 6.5 Hz, 1H), 3.60 (m, 1H), 3.73 (d, J=8.8 Hz, 1H), 3.94 (s, 3H), 4.13 (d, J=13.7 Hz, 1H), 6.91 (d, J=8.8 Hz, 1H), 7.68 (s, 1H), 7.89 (d, J=8.1 Hz, 1H), 8.00 (d, J=2.4 Hz, 1H), 8.16 (d, J=2.7 Hz, 1H), 11.42 (s, 1H), 11.74 (s, 1H); MS(APCl+) m/z 438 (MH+). Anal. calcd for $C_{22}H_{23}N_5O_5 \cdot 2.13H_2O$: C, 55.93; H, 5.77; N, 14.72. Found: C, 55.93; H, 4.88; N, 14.14.

Example 22

Step 1: 5-Bromo-2-(2,6-dimethyl-morpholin-4-yl)-3,4-difluoro-benzaldehyde. 5-Bromo-2,3,4-trifluoro-benzaldehyde (10 g, 41.8 mmol) was dissolved in dry acetonitrile (70 mL). Triethylamine (6.4 mL, 46.0 mmol) was added, followed by trans-2,6-dimethylmorpholine (BASF, 5.3 g, 46 mmol). The mixture was refluxed for 24 hours, then cooled to room temperature, and treated with 1N HCl (58 mL). The acetonitrile was removed by rotoevaporation and the resulting solids were filtered, washed with water then dissolved in THF (100 mL). The solution was dried over MgSO$_4$ and concentrated to a yellow oil. Hexanes were added and the mixture was re-concentrated to give 12.66 g of a yellow powder. 1H NMR (400 MHz, CHLOROFORM-d) d ppm 1.26 (d, J=6.4 Hz, 6H), 2.92 (m, 2H), 3.28 (d, J=11.7 Hz, 2H), 4.15 (m, 2H), 7.78 (dd, J=7.2, 2.3 Hz, 2H), 10.32 (s, 4H).

Step 2: 2-(2,6-Dimethyl-morpholin-4-yl)-3,4-difluoro-5-(4,4,5,5-tetramethyl-[1,3,2]dioxaborolan-2-yl)-benzaldehyde. A solution of 5-Bromo-2-(2,6-dimethyl-morpholin-4-yl)-3,4-difluoro-benzaldehyde (11.6 g, 34.9 mmol) and bis-(pinacolato)diboron (9.3 g, 36.7 mmol) in anhydrous 2-methyl THF (120 mL) was treated with potassium acetate (10 g, 105 mmol) and degassed with argon for 25 minutes. The catalyst Pd(PCy$_3$)$_2$Cl$_2$ (1 g, 1.4 mmol) was then added to the reaction mixture and heated to 80° C. overnight. The reaction was cooled to room temperature and the solids were filtered and washed with THF. The combined filtrate washings were concentrated and dissolved in warm methanol and cooled in the refrigerator overnight. The solids that formed were filtered, washed with cold methanol, and dried to give 4.2 g of a yellow solid.

1H NMR (400 MHz, CHLOROFORM-d) d ppm 1.24 (d, J=6.4 Hz, 6H), 1.1 (s, 12H), 2.95 (m, 2H), 3.35 (m, 2H), 4.16 (m, 2H), 7.94 (dd, J=6.2, 2.0 Hz, 1H), 10.21 (s, 1H).

Step 3: 5-(5-Amino-pyrazin-2-yl)-2-(2,6-dimethyl-morpholin-4-yl)-3,4-difluoro-benzaldehyde. To a suspension of 2-(2,6-Dimethyl-morpholin-4-yl)-3,4-difluoro-5-(4,4,5,5-tetramethyl-[1,3,2]dioxaborolan-2-yl)-benzaldehyde (0.500 g, 1.3 mmol) and cesium carbonate (1.2 g, 3.6 mmol) in previously degassed toluene/IPA/water (4/4/1) mixture (2.5 mL) was added 5-bromo-pyrazin-2-ylamine (Maybridge, 0.208 g, 1.2 mmol) under nitrogen. Tetrakis(triphenylphosphine)palladium-(0) (0.055 g, 0.05 mmol) was added at room temperature and the reaction was heated at 85° C. for 3.5 hrs. The mixture was cooled to room temperature, diluted with EtOAc and water then neutralized. The phases were separated and the aqueous phase was re-extracted with EtOAc (×2). The combined organic layers were dried over MgSO$_4$ and concentrated. Purified by column chromatography eluting with ethyl acetate in hexanes (10-60%) to obtain 150 mgs of product. 1H NMR (400 MHz, CHLOROFORM-d) d ppm 1.28 (d, J=6.4 Hz, 6H), 2.97 (m, 2H), 3.34 (m, 2H), 4.18 (m, 2H), 4.78 (s, 2H), 8.08 (d, J=1.6 Hz, 1H), 8.19 (dd, J=8.4, 2.1 Hz, 1H), 8.44 (m, 1H), 10.37 (s, 1H); MS(APCl+) m/z 349 (MH+).

Step 4: Compound 22. A stirring slurry of 5-(5-Amino-pyrazin-2-yl)-2-(2,6-dimethyl-morpholin-4-yl)-3,4-difluoro-benzaldehyde (0.148 g, 0.425 mmol) in nBuOH was treated with barbituric acid (0.057 g, 0.446 mmol). The reaction mixture was stirred at room temperature for 30 minutes then heated to reflux overnight. Upon cooling a solid precipitate resulted which was filtered. Further analysis indicated that neither the filtrate nor the solid material was pure. The solids and the filtrate were recombined and concentrated then purified by column chromatography eluting with MeOH in DCM (1-12%) to give 112 mgs as an enriched mixture of isomers. 1H NMR (400 MHz, DMSO-d6) Major isomer: d ppm 0.84 (d, J=6.4 Hz, 3H), 1.07 (d, J=6.0 Hz, 3H), 2.84 (d, J=14.4 Hz, 1H), 2.96 (m, 1H), 3.44 (d, J=14.6 Hz, 1H), 3.59 (dd, J=8.6, 6.2 Hz, 1H), 3.71 (m, 1H), 3.77 (d, J=8.8 Hz, 1H), 3.99 (dd, J=13.7, 2.4 Hz, 1H), 6.50 (s, 2H), 7.20 (d, J=8.2 Hz, 1 H), 7.88 (d, J=1.6 Hz, 1H), 8.16 (dd, J=2.4, 1.5 Hz, 1H), 11.40 (s, 1H), 11.74 (s, 1H); MS(APCl+) m/z 459 (MH+).

Example 23

Step 1: 5-(5-Bromo-pyrazin-2-yl)-2-(2,6-dimethyl-morpholin-4-yl)-3,4-difluoro-benzaldehyde. To a suspension of 2-(2,6-Dimethyl-morpholin-4-yl)-3,4-difluoro-5-(4,4,5,5-tetramethyl-[1,3,2]dioxaborolan-2-yl)-benzaldehyde (Example 22, step 2) (1.5 g, 3.9 mmol) and sodium carbonate (1.1 g, 11 mmol) in previously degassed acetonitrile/water (1/1) mixture (4 mL) was added 2-bromo-5-iodo-pyrazine (1.0 g, 3.5 mmol) under nitrogen. Bis-(triphenylphosphine)-dichloro-palladium-(II) (0.099 g, 0.14 mmol) was added at room temperature and the reaction was heated overnight at 55° C. The mixture was cooled to room temperature, diluted with EtOAc and water then neutralized. The phases were separated and the aqueous phase was re-extracted with EtOAc (×2). The combined organic layers were dried over MgSO$_4$ and concentrated. Purified by column chromatography eluting with ethyl acetate in hexanes (5-40%) to obtain 931 mgs of product. 1H NMR (400 MHz, CHLOROFORM-d) d ppm 1.28 (d, J=6.4 Hz, 6H), 3.02 (m, 2H), 3.40 (m, 2H), 4.19 (m, 2H), 8.28 (dd, J=8.2, 2.1 Hz, 1H), 8.74 (d, J=1.4 Hz, 1H), 8.78 (m, 1H), 10.29 (s, 1H) ; MS(APCl+) m/z 412, 414 (MH+).

Step 2: 2-(2,6-Dimethyl-morpholin-4-yl)-3,4-difluoro-5-(5-methyl-pyrazin-2-yl)-benzaldehyde. To a suspension of 5-(5-Bromo-pyrazin-2-yl)-2-(2,6-dimethyl-morpholin-4-yl)-3,4-difluoro-benzaldehyde (0.375 g, 0.91 mmol) and sodium carbonate (0.29 g, 2.7 mmol) in previously degassed acetonitrile/water (1/1) mixture (4 mL) was added methyl boronic acid (0.11 g, 1.8 mmol) under nitrogen. Bis-(triphenylphosphine)-dichloro-palladium-(II) (0.026 g, 0.036 mmol) was added at room temperature and the reaction was heated for 5 hours at 85° C. Analysis indicated that starting material had not fully been consumed so an additional 1 equivalent of methyl boronic acid was added to the reaction and stirred overnight at 85° C. The mixture was cooled to room temperature, diluted with EtOAc and water then neutralized. The phases were separated and the aqueous phase was re-extracted with EtOAc (×2). The combined organic layers were dried over MgSO$_4$ and concentrated. Purified by column chromatography eluting with ethyl acetate in hexanes (5-35%) to obtain 132 mgs of product. 1H NMR (400 MHz, CHLOROFORM-d) d ppm 1.28 (d, J=6.4 Hz, 6H), 2.61 (s, 3H), 3.00 (m, 2H), 3.38 (m, 2 H), 4.19 (m, 2H), 8.26 (dd, J=8.2, 2.1 Hz, 1H), 8.54 (d, J=1.2 Hz, 1H), 8.89 (dd, J=2.3, 1.6 Hz, 1H), 10.33 (s, 1H); MS(APCl+) m/z 348 (MH+).

Step 3: Compound 23. A stirring solution of 2-(2,6-Dimethyl-morpholin-4-yl)-3,4-difluoro-5-(5-methyl-pyrazin-2-yl)-benzaldehyde (0.185 g, 0.533 mmol) in acetic acid, glacial (4 mL) was treated with barbituric acid (0.072 g, 0.559 mmol). The reaction mixture was stirred for 1 hour at 110° C. then slowly cooled to room temperature. Reaction mixture was azeotroped and concentrated using toluene. Purified by column chromatography eluting with ethyl acetate in hexanes (25-80%) to obtain 99 mgs of product. 1H NMR (400 MHz, DMSO-d6) d ppm 0.85 (d, J=6.4 Hz, 3H), 1.08 (d, J=6.2 Hz, 3H), 2.45 (s, 3H), 2.86 (d, J=14.4 Hz, 1H), 3.01 (m, 1H), 3.51 (d, J=14.4 Hz, 1H), 3.60 (dd, J=8.8, 6.4 Hz, 1H), 3.72 (m, 1H), 3.81 (d, J=8.8 Hz, 1H), 4.03 (dd, J=13.5, 2.0 Hz, 1H), 7.36 (d, J=7.2 Hz, 1H), 8.53 (d, J=1.2 Hz, 1H), 8.75 (m, 1H), 11.44 (s, 1H), 11.77 (s, 1H); MS(APCl+) m/z 458 (MH+). Anal. calcd for $C_{22}H_{21}F_2N_5O_4 \cdot 0.14H_2O$: C, 57.45; H, 4.66; N, 15.23. Found: C, 57.14; H, 4.55; N, 14.83.

Example 24

Compound 24. A stirring slurry of 5-(5-Bromo-pyrazin-2-yl)-2-(2,6-dimethyl-morpholin-4-yl)-3,4-difluoro-benzaldehyde (Example 23, step 1) (0.274 g, 0.665 mmol) in nBuOH was treated with barbituric acid (0.089 g, 0.698 mmol). The reaction mixture was stirred at room temperature for 30 minutes then heated to 105° C. overnight. The dark red solution was concentrated in vacuo to a reddish oil which was azeotroped with toluene to give an enriched mixture of isomers. 1H NMR (400 MHz, DMSO-d6) Major isomer: d ppm 0.85 (d, J=6.4 Hz, 3H), 1.08 (d, J=6.2 Hz, 3H), 2.86 (d, J=14.6 Hz, 1H), 3.02 (m, 1 H), 3.53 (d, J=14.6 Hz, 1H), 3.60 (dd, J=8.7, 6.5 Hz, 1H), 3.72 (m, 1H), 3.83 (d, J=8.8 Hz, 1H), 4.04 (dd, J=13.6, 1.9 Hz, 1H), 7.39 (d, J=8.2 Hz, 1H), 8.71 (t, J=1.7 Hz, 1H), 8.82 (d, J=1.6 Hz, 1H), 11.45 (s, 1H), 11.78 (s, 1H); MS(APCl+) m/z 522, 524 (MH+).

Example 25

Step 1. 2-iodo-5-methoxy-pyrazine. Sodium methoxide (25% wt. in MeOH, 0.321 mL, 1.4 mmol) was combined with N-methyl pyrrolidine (NMP) (1.28 mL) and warmed to 60° C. 2-bromo-5-iodo-pyrazine (0.40 g, 1.4 mmol) was added. The suspension was stirred at 60° C. for 1 hour. Combined with an additional 100 mg previously run reaction prior to work-up. Reaction mixture was partitioned between H$_2$O and ethyl acetate and the aqueous layer was extracted (3×) with ethyl acetate. The combined extracts were dried over MgSO$_4$, filtered and concentrated to give a brown oil which solidified to obtain 406 mgs of crude material. 1H NMR (400 MHz, CHLOROFORM-d) d ppm 3.90 (s, 3H), 8.03 (d, J=1.4 Hz, 1H), 8.29 (d, J=1.4 Hz, 1H); MS (APCl+, m/z) 237.

Step 2. 2-(2,6-Dimethyl-morpholin-4-yl)-3,4-difluoro-5-(5-methoxy-pyrazin-2-yl)-benzaldehyde. To a suspension of 2-(2,6-Dimethyl-morpholin-4-yl)-3,4-difluoro-5-(4,4,5,5-tetramethyl-[1,3,2]dioxaborolan-2-yl)-benzaldehyde (0.78 g, 2.0 mmol) and sodium carbonate (0.54 g, 5.1 mmol) in previously degassed acetonitrile/water (3 mL/3 mL) mixture was added 2-iodo-5-methoxy-pyrazine (0.40 g, 1.69 mmol) under nitrogen. Bis-(triphenylphosphine)-dichloro-palladium-(II) (0.048 g, 0.068 mmol) was added at room temperature and the reaction was heated overnight at 60° C. The mixture was cooled to room temperature, diluted with EtOAc and water. The phases were separated and the aqueous phase was re-extracted with EtOAc (3×). The combined extracts were dried over MgSO$_4$ and purified by column chromatography 0-5% EA/Hex to obtain 386 mgs of solid. 1H NMR (400 MHz, CHLOROFORM-d) d ppm 1.28 (d, J=6.4 Hz, 6H), 2.98 (m, 2 H), 3.35 (m, 2H), 3.99 (s, 3H), 4.18 (m, 2H), 8.22 (dd, J=8.2, 2.1 Hz, 1H), 8.29 (d, J=1.4 Hz, 1H), 8.53 (dd, J=2.2, 1.5 Hz, 1H), 10.35 (s, 1H); MS (APCl+, m/z) 364.

Step 3. Compound 25. A stirring solution of 2-(2,6-Dimethyl-morpholin-4-yl)-3,4-difluoro-5-(5-methoxy-pyrazin-2-yl)-benzaldehyde (0.386 g, 1.06 mmol) was dissolved in acetic acid (3 mL):H$_2$O (2 mL) treated with barbituric acid (0.143 g, 1.12 mmol). The reaction mixture was stirred for 1 hour at 110° C. then slowly cooled to room temperature. The precipitate was filtered to obtain 388 mgs of a light brown solid. 1H NMR (400 MHz, DMSO-d6) d ppm 0.85 (d, J=6.4 Hz, 3H), 1.08 (d, J=6.2 Hz, 3H), 2.86 (d, J=14.2 Hz, 1 H), 2.99 (m, 1H), 3.48 (d, J=13.6 Hz, 1H), 3.60 (dd, J=8.8, 6.4 Hz, 1H), 3.71 (m, 1H), 3.80 (d, J=8.8 Hz, 1H), 3.89 (s, 3H), 4.01 (dd, J=13.5, 2.2 Hz, 1H), 7.29 (d, J=7.8 Hz, 1 H), 8.31 (d, J=1.6 Hz, 1H), 8.44 (dd, J=2.2, 1.5 Hz, 1H), 11.42 (s, 1H), 11.76 (s, 1H); MS (APCl+, m/z) 474. Anal. calcd for $C_{22}H_{21}F_2N_5O_5 \cdot 0.08CH_3CO_2H$: C, 55.65; H, 4.49; N, 14.64. Found: C, 55.49; H, 4.22; N, 14.25.

Example 26

Step 1. 2-ethoxy-5-iodo-pyrazine. Sodium ethoxide (21% wt., 0.524 mL, 1.4 mmol) was combined with NMP (2 mL) and warmed to 60° C. 2-bromo-5-iodo-pyrazine (0.40 g, 1.4 mmol) was then added. The suspension was stirred at 60° C. for 1 hour. Reaction mixture was partitioned between H$_2$O and ethyl acetate and the aqueous layer was extracted (3×) with ethyl acetate. The combined extracts were dried over MgSO$_4$, filtered and concentrated to give a brown oil (362 mgs). 1H NMR (400 MHz, CHLOROFORM-d) d ppm 1.36 (t, J=7.1 Hz, 3H), 4.31 (q, J=7.0 Hz, 2H), 8.00 (d, J=1.6 Hz, 1H), 8.26 (d, J=1.6 Hz, 1H); MS (APCl+, m/z) 251.

Step 2. 2-(2,6-Dimethyl-morpholin-4-y2)-5-(5-ethoxy-pyrazin-2-yl)-3,4-difluoro-benzaldehyde. To a suspension of 2-(2,6-Dimethyl-morpholin-4-yl)-3,4-difluoro-5-(4,4,5,5-tetramethyl-[1,3,2]dioxaborolan-2-yl)-benzaldehyde (0.66 g, 1.7 mmol) and sodium carbonate (0.61 g, 5.8 mmol) in previously degassed acetonitrile/water (3 mL/3 mL) mixture was added 2-ethoxy-5-iodo-pyrazine (0.362 g, 1.45 mmol) under nitrogen. Bis-(triphenylphosphine)-dichloro-palladium-(II) (0.041 g, 0.058 mmol) was added at room temperature and the reaction was heated overnight at 60° C. The mixture was cooled to room temperature, diluted with EtOAc and water. The phases were separated and the aqueous phase was re-extracted with EtOAc (3×). The combined extracts were dried over MgSO$_4$ and purified by column chromatography 0-5% EA/Hex to obtain 313 mgs of solid. 1H NMR (400 MHz, CHLOROFORM-d) d ppm 1.28 (d, J=6.4 Hz, 6H), 1.41 (t, J=7.1 Hz, 3H), 2.98 (m, 2H), 3.36 (m, 2H), 4.18 (m, 2H), 4.41 (q, J=7.1 Hz, 2H), 8.22 (dd, J=8.2, 2.1 Hz, 1H), 8.26 (d, J=1.4 Hz, 1H), 8.51 (dd, J=2.3, 1.6 Hz, 1H), 10.36 (s, 1 H); MS (APCl+, m/z) 378.

Step 3. Compound 26. A stirring solution of 2-(2,6-Dimethyl-morpholin-4-yl)-5-(5-ethoxy-pyrazin-2-yl)-3,4-difluoro-benzaldehyde (0.312 g, 0.829 mmol) dissolved in acetic acid (2.48 mL):H$_2$O (1.65 mL) was treated with barbituric acid (0.112 g, 0.871 mmol). The reaction mixture was stirred for 1 hour at 110° C. then slowly cooled to room temperature. The reaction mixture was azeotroped, concentrated using toluene. The mixture was purified by column chromatography eluting with ethyl acetate in hexanes to obtain 320 mgs of product. 1H NMR (400 MHz, DMSO-d6) d ppm 0.85 (d, J=6.4 Hz, 3H), 1.07 (d, J=6.0 Hz, 3H), 1.31 (t, J=7.1 Hz, 3H), 2.86 (d, J=14.4 Hz, 1H), 2.99 (m, 1 H), 3.48 (d, J=14.2 Hz, 1H), 3.60 (dd, J=8.7, 6.3 Hz, 1H), 3.71 (m, 1H), 3.79 (d, J=8.8 Hz, 1H), 4.01 (dd, J=13.5, 2.2 Hz, 1H), 4.33 (q, J=7.0 Hz, 2H), 7.28 (d, J=8.0 Hz, 1H), 8.28 (d, J=1.4 Hz, 1H), 8.42 (m, 1H), 11.42 (s, 1H), 11.76 (s, 1H); MS (APCl+, m/z) 488. Anal. calcd for $C_{22}H_{21}F_2N_5O_5 \cdot 0.11CH_3CO_2H$: C, 56.45; H, 4.78; N, 14.18. Found: C, 56.21; H, 4.68; N, 13.79.

Example 27

In this example, the in vitro antibacterial activity of selected compounds was determined against *S. aureus* and *H. influenzae*. Except for clarifying or modifying statements, MIC testing followed procedures recommended by the NCCLS[1-2] or followed the descriptions cited below.

Bacterial Cultures At least the following organisms are included in the screen: *Staphylococcus aureus* SA-1 (UC-76) and *H. influenzae* HI-3542. Incubations were at 35° C. Stock bacterial cultures were maintained on Tryptic Soy Agar containing 5% Sheep Blood (BD, Becton Dickinson Microbiology Systems, Cockeysville, Md.), anaerobes were maintained on Anaerobic Blood Agar plates—CDC Formulation (BD), and fastidious organisms were maintained on Chocolate Agar II Plates (BD). Specific conditions of handling are listed below.

Permanent Stock Culture Collection Stock cultures are stored as frozen suspensions at −70° C. Most cultures are routinely suspended in 10% skim milk (BD) prior to snap freezing in dry ice/ethanol and then placed in a −70° C. freezer. *Haemophilus* were suspended in inactivated horse serum (Colorado Serum Company, Denver, Colo.) containing 7.5% glucose prior to snap freezing.

Maintenance of Stock Cultures Most cultures were maintained on Tryptic Soy Agar containing 5% Sheep Blood at room temperature (20° C.). Each culture was recovered from frozen and transferred an additional time before MIC testing. Fresh plates were inoculated the day before testing, incubated overnight, and checked to confirm purity and identity.

*Haemophilus* was maintained on Chocolate Agar II Plates at room temperature in a candle jar providing a 3 5% CO$_2$ atmosphere.

Confirming Identity of Cultures Culture identifications were confirmed by standard microbiological methods[3]. Cultures were streaked onto appropriate agar plates for visualization of purity, expected colony morphology, and hemolytic patterns. Gram stains were also utilized.

The identities of recent isolates used in this test were confirmed using a MicroScan WalkAway 40 SI Instrument (Dade Behring, West Sacramento, Calif.). This device utilizes an automated incubator, reader, and computer to assess for identification purposes the biochemical reactions carried out by each organism. Using this machine, organism identification (confirmation) and an initial antibiogram was generated for each strain.

Standardized Organism Inocula Frozen stock cultures were used as the initial source of organisms for performing microbroth dilution MIC testing. Stock cultures were passed on their standard growth medium for at least 1 growth cycle (18 24 hours) prior to their use.

Most bacteria, unless otherwise noted, were prepared directly from agar plates in 10 mL aliquots of the appropriate broth medium. Bacterial cultures were adjusted to the opacity of a 0.5 McFarland Standard (optical density value of 0.28-0.33 on a Perkin-Elmer Lambda EZ150 Spectrophotometer Wellesley, Mass., set at a wavelength of 600 nm).). The adjusted cultures were diluted 400 fold (0.25 mL inoculum+ 100 mL broth) in growth media to produce a starting suspension of approximately $5 \times 10_5$ colony forming units (CFU)/mL. Unless otherwise noted, bacterial strains were tested in cation adjusted Mueller Hinton Broth (CAMHB).

*Haemophilus influenzae* strains were grown on Chocolate Agar II Plates and tested in *Haemophilus* Test Medium (Remel, Lenexa, Kans.).

Test Compound ("Drug") Preparation Compounds were solubilized in DMSO. Drug stock solutions were prepared on the day of testing. Drugs were weight corrected for assay content where necessary.

Drug Dilution Tray Preparation Microbroth dilution stock plates were prepared in two dilution series, 64 to 0.06 µg drug/mL and 0.25 to 0.00025 µg drug/mL. For the high concentration series, 200 µL of stock solution (2 mg/mL) was added to duplicate rows of a 96-well microtiter plate. This was used as the first well in the dilution series. Serial two-fold decremental dilutions were made using a BioMek FX robot (Beckman Coulter Inc., Fullerton, Calif.) with 10 of the remaining 11 wells, each of which contained 100 µL of the appropriate solvent/diluent. Row 12 contained solvent/diluent only and served as the control. For tube one of the low concentration series, 200 µL of an 8 µg/mL stock was added to duplicate rows of a 96-well plate. Serial two-fold dilutions were made as described above.

Daughter plates were spotted (3.2 µL/well) from the stock plates listed above using the BioMek FX robot and were either used immediately or frozen at −70° C. until use.

Plate Inoculation Aerobic organisms were inoculated (100 µL volumes) into the thawed plates using the BioMek FX robot. The inoculated plates were placed in stacks of no more than 5 and covered with an empty plate. These plates were incubated 16 to 24 hours in ambient atmosphere according to CLSI guidelines[2].

Reading the Test After inoculation and incubation, the degree of bacterial growth was estimated visually with the aid of a Test Reading Mirror (Dynex Technologies 220 16) in a darkened room with a single light shining directly through the top of the microbroth tray. The MIC was the lowest concentration of drug that prevented macroscopically visible growth under the conditions of the test. Testing was performed in duplicate. When the MIC values in duplicate tests varied by 1 well (2 fold), the lower values were reported. If the MICs varied by 2 dilutions, the middle value was reported. Greater than this 4 fold variance called for the test to be repeated, after which a similar determination was applied to all values.

REFERENCES

1. National Committee for Clinical Laboratory Standards. Performance Standards for Antimicrobial Susceptibility Testing; Fourteenth Informational Supplement. NCCLS document M100-S14 {ISBN 1-56238-516-X}, NCCLS, 940 West Valley Road, Suite 1400, Wayne, Pa. 19087-1898 USA, 2004.

2. National Committee for Clinical Laboratory Standards. Methods for Dilution Antimicrobial Tests for Bacteria That Grow Aerobically; Approved Standard-Sixth Edition. NCCLS document M7-A6 {ISBN 1-56238-486-4}, NCCLS, 940 West Valley Road, Suite 1400, Wayne, Pa. 19087-1898 USA, 2003.

3. Murray P R, Baron E J, Jorgensen J H, Pfaller M A, Yolken R H. Manual of Clinical Microbiology, Eighth Edition. ASM Press {ISBN 1-55581-255-4}, American Society for Microbiology, 1752 N Street NW, Washington, DC 20036-2904 USA, 2003.

Using this protocol, the following results were generated:

TABLE 2

Minimum Inhibitory Concentration (μg/ml)

| Compound/ Example No. | S. aureus UC76 | H. influenzae 3542 |
|---|---|---|
| 1 | 0.25 | 1 |
| 2 | 0.125 | 0.5 |
| 3 | 32 | >64 |
| 4 | 0.25 | 0.5 |
| 5 | 0.5 | 1 |
| 6 | 0.5 | 0.25 |
| 7 | ND* | ND |
| 8 | ND | ND |
| 9 | ND | ND |
| 10 | ND | ND |
| 11 | ND | ND |
| 12 | ND | ND |
| 13 | ND | ND |
| 14 | ND | ND |
| 15 | 1 | 4 |
| 16 | >64 | >64 |
| 17 | >64 | >64 |
| 18 | >64 | >64 |
| 19 | 2 | 2 |
| 20 | 4 | 2 |
| 21 | 16 | 32 |
| 22 | 0.5 | 0.5 |
| 23 | 0.125 | 1 |
| 24 | ND | ND |
| 25 | 0.125 | 0.5 |
| 26 | 0.25 | 1 |

*ND—not determined

Relative stereochemistry for racemic compounds was assigned based on the R or S designation of the structures as set forth in Table 1.

As used herein, reference to "a" or "an" means "one or more." Throughout, the plural and singular should be treated as interchangeable, other than the indication of number.

As will be understood by one skilled in the art, for any and all purposes, particularly in terms of providing a written description, all ranges disclosed herein also encompass any and all possible subranges and combinations of subranges thereof as well as the individual values making up the range, particularly integer values. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. For example, the range $C_1$-$C_6$, includes the subranges $C_2$-$C_6$, $C_3$-$C_6$, $C_3$-$C_5$, $C_4$-$C_6$, etc., as well as $C_1$ (methl), $C_2$ (ethyl), $C_3$ (propyl), $C_4$ (butyl), $C_5$ (pentyl) and $C_6$ (hexyl) individually. As will also be understood by one skilled in the art, all language such as "up to," "at least," "greater than," "less than," "more than," "or more" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Additionally, for all purposes, the present invention encompasses not only the main group, but also the main group absent one or more of the group members. The present invention also envisages the explicit exclusion of one or more of any of the group members in the claimed invention.

As will be understood by the skilled artisan, all numbers, including those expressing quantities of ingredients, properties such as molecular weight, reaction conditions, and so forth, are approximations and understood as being modified in all instances by the term "about." These values can vary depending upon the desired properties sought to be obtained by those skilled in the art utilizing the present teachings of the present invention. It is also understood that such values inherently contain variability necessarily resulting from the standard deviations found in their respective testing measurements.

All references disclosed herein are specifically incorporated herein by reference thereto.

While specific embodiments have been illustrated and described, it should be understood that these embodiments do not limit the scope of the invention and that changes and modifications can be made in accordance with ordinary skill in the art without departing from the invention in its broader aspects as defined in the following claims. Reference to a "step" in the application is used for convenience purposes only and does not categorize, define or limit the invention as set forth herein.

What is claimed is:

1. A compound of formula I:

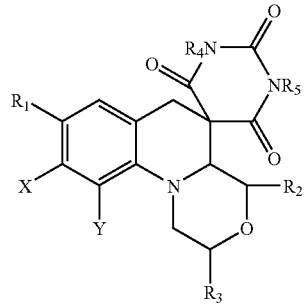

or a salt, solvate, or a hydrate thereof,
wherein:
$R_1$ is pyrazine,

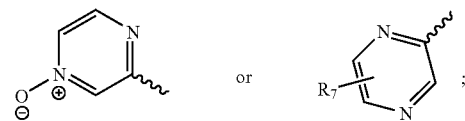

∿∿∿ indicates a point of attachment;

$R_7$ is H, halo, $C_{1-6}$ alkyl, $C_3$-$C_8$ cycloalkyl, heterocyclyl, ether, —CN, —$NR_8R_9$, —$OR_{10}$, —$(CH_2)_mOPO_3(R_p)_2$, —$(CH_2)_mOC(=O)(CH_2)_mCH_3$, —$(CH_2)_mOC(=O)$ $(CH_2)_mCO_2R_6$, —$(CH_2)_mOC(=O)(CH_2)_mNR_8R_9$, —$(CH_2)_mOC(=O)E$, —$(CH_2)_mCO_2(CH_2)_mCH_3$, —$(CH_2)_mCO_2(CH_2)_mCO_2R_6$, —$(CH_2)_mCO_2(CH_2)_m$ $NR_8R_9$, —$(CH_2)_mCO_2E$, —$(CH_2)_mC(=O)NR_6(CH_2)_m$ $CO_2R_6$, —$(CH_2)_mC(=O)NR_8R_9$, —$(CH_2)_mNR_8R_9$, —$(CH_2)_mPO_3(R_{11})_2$, —$(CH_2)_mOR_{10}$, which is optionally substituted with —$OR_{11}$, —$(CH_2)_mC(=O)OR_{11}$, —$(CH_2)_mNR_{11}SO_nR_{12}$, —$(CH_2)_mSO_nR_{12}$, —$(CH_2)_m$ $SO_nNR_8R_9$, aryl, or heteroaryl;

each n is independently is 0, 1 or 2;

$R_{10}$ is H, $C_{1-6}$ alkyl, —$PO_3H_2$, C(=O)$R_{13}$, C(=O)O$R_{13}$ or C(=O)N$R_8R_9$ and $R_{11}$, $R_{12}$ and $R_{13}$ are independently H, $C_{1-6}$ alkyl, aminoalkyl, benzyl, phenyl, an amino acid residue or a peptide residue;

$R_2$ and $R_3$ are independently H or $C_{1-6}$ alkyl;

$R_4$ and $R_5$ are independently H, $C_{1-6}$ alkyl which is optionally substituted with halo, ether, —$(CH_2)_m$aryl, benzyl, —O$(CH_2)_m$aryl, —Obenzyl, —$(CH_2)_m NR_8R_9$, —$(CH_2)_m OR_6$, —$(CH_2)_m OPO_3(R_p)_2$, —$(CH_2)_m OC(=O)(CH_2)_m CH_3$, —$(CH_2)_m OC(=O)(CH_2)_m CO_2R_6$, —$(CH_2)_m OC(=O)(CH_2)_m NR_8R_9$, —$(CH_2)_m OC(=O)E$, or $R_4$ and $R_5$ together with the atoms to which they are attached form a heterocyclic ring;

each m is independently 0, 1, 2 or 3;

E is an ether;

each $R_p$ is independently H, $C_{1-6}$ alkyl, benzyl, phenyl, or $(R_p)_2$ together with the atoms to which they are attached form a heterocyclic ring;

each $R_6$ is independently H, $C_{1-6}$ alkyl, $C_{1-6}$ acyl or benzyl;

$R_8$ and $R_9$ are independently H, $C_{1-6}$ alkyl or $R_8$ and $R_9$ together with the atom to which they are attached form a heterocyclic ring which is optionally substituted with $C_{1-6}$ alkyl; and X and Y are independently H, halo, $C_{1-6}$ alkyl, —$OR_6$, —CN, a ether which is optionally substituted with halo, a heterocyclyl, or a amine.

2. The compound of claim 1 or a salt, solvate, or a hydrate thereof, wherein X is H or F, Y is H or F or both X and Y are H or F.

3. The compound of claim 2 or a salt, solvate, or a hydrate thereof, wherein $R_2$ and $R_3$ are methyl.

4. The compound of claim 3 or a salt, solvate, or a hydrate thereof, wherein $R_1$ is

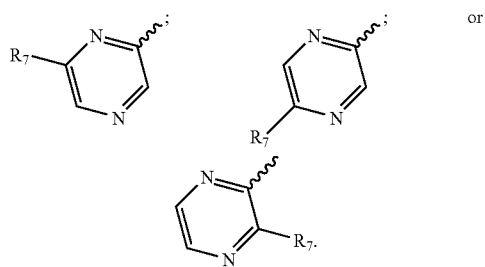

5. The compound of claim 4 or a salt, solvate, or a hydrate thereof, wherein $R_7$ is H or methyl.

6. The compound of claim 5 having formula Ib:

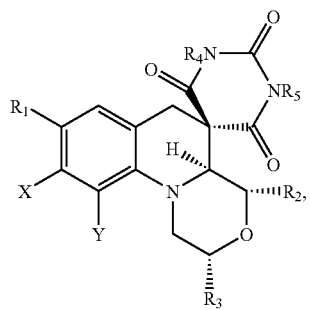

or a salt, solvate, or a hydrate thereof.

7. The compound of claim 1 or a salt, solvate, or a hydrate thereof, wherein each E or ether independently has the formula —$[(CV_2)_p O(CV_2)_p]_q CH_3$ wherein each p is independently 0, 1, 2, 3, 4, 5 or 6, each q is independently 1, 2, 3, 4, 5 or 6, each V is independently H or another —$[(CV_2)_p O(CV_2)_p]_q CH_3$.

8. The compound of claim 7 or a salt, solvate, or a hydrate thereof, wherein each E or ether independently has the formula —$[(CH_2)_p O(CH_2)_p]_q CH_3$ where each p is independently 0, 1, 2, 3 or 4 and each q is independently 1, 2, 3 or 4.

9. The compound of claim 1 wherein said compound is selected from the group consisting of:

rel-(2S,4R,4aR)-9,10-difluoro-2,4-dimethyl-8-pyrazin-2-yl-1,2,4,4a-tetrahydro-2'H, 6H spiro[1,4-oxazino[4,3-a]quinoline-5,5'-pyrimidine]-2',4',6'(1'H,3'H)-trione;

(2R,4S,4aS)-9,10-difluoro-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione;

(2S,4R,4aR)-9,10-difluoro-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione;

(2R,4S,4aS)-9,10-difluoro-2,4-dimethyl-1',3'-bis(morpholin-4-ylmethyl)-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione;

(2R,4S,4aS)-9,10-difluoro-2,4-dimethyl-1',3'-bis[(4-methylpiperazin-1-yl)methyl]-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione;

(2R,4S,4aS)-9,10-difluoro-2,4-dimethyl-8-(4-oxidopyrazinpyrazin-2-yl)-1,2,4,4a-tetrahydro-2'H,6H-spiro[1,4-oxazino[4,3-a]quinoline-5,5'-pyrimidine]-2',4',6'(1'H,3'H)-trione;

rel-(2S,4R,4aR)-9,10-difluoro-2,4-dimethyl-2',4',6'-trioxo-8-pyrazin-2-yl-1,2,4,4a-tetrahydro-2'H,6H-spiro[1,4-oxazino[4,3-a]quinoline-5,5'-pyrimidine]-1',3'(4'H,6'H)-diyl]bis(methylene)diacetate;

(2S,4R,4aR)-9,10-difluoro-2,4-dimethyl-2',4',6'-trioxo-8-pyrazin-2-yl-1,2,4,4a-tetrahydro-2'H,6H-spiro[1,4-oxazino[4,3-a]quinoline-5,5'-pyrimidine]-1',3'(4'H,6'H)-diyl]bis(methylene)diacetate;

rel-(2S,4R,4aR)-9,10-difluoro-1',3'-bis(hydroxymethyl)-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione;

(2S,4R,4aR)-9,10-difluoro-1',3'-bis(hydroxymethyl)-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione;

rel-(2S,4R,4aR)-1',3'-bis(chloromethyl)-9,10-difluoro-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione;

rel-tetrabenzyl [(2S,4R,4aR)-9,10-difluoro-2,4-dimethyl-2',4',6'-trioxo-8-pyrazin-2-yl-1,2,4,4a-tetrahydro-2'H,6H-spiro[1,4-oxazino[4,3-a]quinoline-5,5'-pyrimidine]-1',3'(4'H,6'H)-diyl]bis(methylene)bis(phosphate);

(2S,4R,4aR)-1',3'-bis(bromomethyl)-9,10-difluoro-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione;

tetra-tert-butyl [(2S,4R,4aR)-9,10-difluoro-2,4-dimethyl-2',4',6'-trioxo-8-pyrazin-2-yl-1,2,4,4a-tetrahydro-2'H,6H-spiro[1,4-oxazino[4,3-a]quinoline-5,5'-pyrimidine]-1',3'(4'H,6'H)-diyl]bis(methylene)bis(phosphate);

rel-(2S,4R,4aR)-10-fluoro-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione;

rel-(2S,4R,4aR)-10-fluoro-2,4-dimethyl-9-morpholin-4-yl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione;

rel-(2S,4R,4aR)-10-fluoro-9-(2-methoxyethoxy)-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione;

rel-(2S,4R,4aR)-10-fluoro-9-(2-fluoroethoxy)-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione;

rel-(2S,4R,4aR)-9-fluoro-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione;

rel-(2S,4R,4aR)-2,4-dimethyl-8-pyrazin-2-yl-1,2,4,4a-tetrahydro-2'H,6H-spiro[1,4-oxazino[4,3-a]quinoline-5,5'-pyrimidine]-2',4',6'(1'H,3'H)-trione;

rel-(2S,4R,4aR)-8-(3-methoxypyrazin-2-yl)-2,4-dimethyl-1,2,4,4a-tetrahydro-2'H,6H-spiro[1,4-oxazino[4,3-a]quinoline-5,5'-pyrimidine]-2',4',6'(1'H,3'H)-trione;

(2R,4S,4aS)-8-(5-aminopyrazin-2-yl)-9,10-difluoro-2,4-dimethyl-1,2,4,4a-tetrahydro-2'H,6H-spiro[1,4-oxazino[4,3-a]quinoline-5,5'-pyrimidine]-2',4',6'(1'H,3'H)-trione;

(2R,4S,4aS)-9,10-difluoro-2,4-dimethyl-8-(5-methylpyrazin-2-yl)-1,2,4,4a-tetrahydro-2'H,6H-spiro[1,4-oxazino[4,3-a]quinoline-5,5'-pyrimidine]-2',4',6'(1'H,3'H)-trione;

(2R,4S,4aS)-8-(5-bromopyrazin-2-yl)-9,10-difluoro-2,4-dimethyl-1,2,4,4a-tetrahydro-2'H,6H-spiro[1,4-oxazino[4,3-a]quinoline-5,5'-pyrimidine]-2',4',6'(1'H,3'H)-trione;

(2R,4S,4aS)-9,10-difluoro-8-(5-methoxypyrazin-2-yl)-2,4-dimethyl-1,2,4,4a-tetrahydro-2'H,6H-spiro[1,4-oxazino[4,3-a]quinoline-5,5'-pyrimidine]-2',4',6'(1'H,3'H)-trione; and (2R,4S,4aS)-8-(5-ethoxypyrazin-2-yl)-9,10-difluoro-2,4-dimethyl-1,2,4,4a-tetrahydro-2'H,6H-spiro[1,4-oxazino[4,3-a]quinoline-5,5'-pyrimidine]-2',4',6'(1'H,3'H)-trione;

or an enantiomer or diastereomer thereof or a salt, solvate, or hydrate thereof.

10. The compound of claim 1 wherein said compound is (2R,4S,4aS)-9,10-difluoro-2,4-dimethyl-8-(5-methylpyrazin-2-yl)-1,2,4,4a-tetrahydro-2'H,6H-spiro[1,4-oxazino [4,3-a]quinoline-5,5'-pyrimidine]-2',4',6'(1'H,3'H)-trione, or an enantiomer or diastereomer thereof or a salt, solvate, or hydrate thereof.

11. The compound of claim 1 wherein said compound is (2R,4S,4aS)-9,10-difluoro-2,4-dimethyl-8-(5-methylpyrazin-2-yl)-1,2,4,4a-tetrahydro-2'H, 6H-spiro[1,4-oxazino[4,3-a]quinoline-5,5'-pyrimidine]-2',4',6'(1'H,3'H)-trione, or a salt, solvate, or a hydrate thereof.

12. A pharmaceutical composition comprising a compound of claim 1 and a pharmaceutically acceptable carrier, diluent or excipient.

13. A method of making a compound of claim 1 having formula Ia comprising:

(a) reacting a compound of formula IIIa with a compound of formula IV at a temperature sufficient to produce a compound of formula Ia:

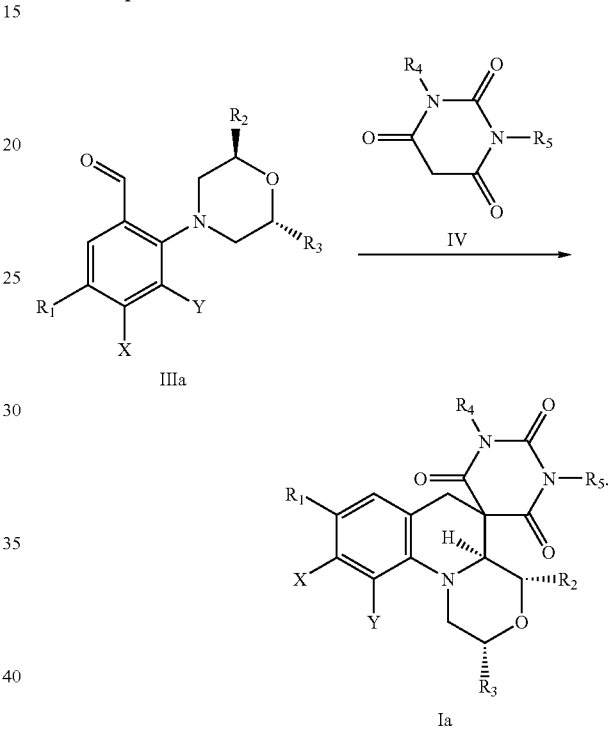

14. The method of claim 13 wherein (a) occurs in an aqueous or organic solvent.

15. The method of claim 14 wherein temperature of (a) is about 60 to about 180° C.

16. The method of claim 15 wherein (a) is performed for about 30 minutes to about 24 hours.

* * * * *